United States Patent
Lowe et al.

(10) Patent No.: US 10,456,320 B2
(45) Date of Patent: Oct. 29, 2019

(54) HAND AND FOOT WRAPS

(71) Applicant: CoolSystems, Inc., Concord, CA (US)

(72) Inventors: Mark H. Lowe, Danville, CA (US); Tamara L. Schirrmacher, Alameda, CA (US); Bryan D. Huff, Vacaville, CA (US)

(73) Assignee: CoolSystems, Inc., Concord, CA (US)

( * ) Notice: Subject to any disclaimer, the term of this patent is extended or adjusted under 35 U.S.C. 154(b) by 982 days.

(21) Appl. No.: 14/502,742

(22) Filed: Sep. 30, 2014

(65) Prior Publication Data

US 2015/0150717 A1    Jun. 4, 2015

Related U.S. Application Data

(60) Provisional application No. 61/885,440, filed on Oct. 1, 2013.

(51) Int. Cl.
*A61H 9/00* (2006.01)
*A61F 7/02* (2006.01)
(Continued)

(52) U.S. Cl.
CPC ............... *A61H 9/005* (2013.01); *A61F 7/02* (2013.01); *A61H 1/008* (2013.01); *A61H 9/0092* (2013.01); *A61F 2007/0034* (2013.01); *A61F 2007/0036* (2013.01); *A61F 2007/0045* (2013.01); *A61F 2007/0054* (2013.01); *A61F 2007/0091* (2013.01); *A61H 2201/0103* (2013.01); *A61H 2201/0242* (2013.01)

(58) Field of Classification Search
CPC .... A61H 9/005; A61H 9/0078; A61H 9/0092; A61H 9/00; A61H 2201/0103; A61H 2201/0242; A61H 2201/1635; A61H 2003/006; A61H 2205/065; A61H 2205/06; A61F 2007/0034; A61F 2007/0054; A61F 2007/0036
USPC ............... 128/845, 878–881; 602/13, 20–22, 602/60–64
See application file for complete search history.

(56) References Cited

U.S. PATENT DOCUMENTS 1,886,768 A    11/1932 Watson
1,958,899 A    5/1934 MacAdams
(Continued)

FOREIGN PATENT DOCUMENTS

CN    2304378 Y    1/1999
CN    1373649 A    10/2002
(Continued)

OTHER PUBLICATIONS

Cothera LLC; VPULSE System Users Manual; 100149 Rev E; © 2013; 18 pgs. (manual rev. dated Jul. 2013).
(Continued)

*Primary Examiner* — Colin W Stuart
*Assistant Examiner* — Douglas Y Sul
(74) *Attorney, Agent, or Firm* — Meunier Carlin & Curfman LLC

(57) ABSTRACT

A device for providing thermal treatment to a patient's hand is provided. The device includes a therapy component for applying thermal therapy, compression therapy, or both; a sleeve for receiving the therapy device and sized and shaped to cover the patient's hand; and a hand support for supporting the patient's hand in a relaxed state.

38 Claims, 25 Drawing Sheets

(51) Int. Cl.
   *A61H 1/00*      (2006.01)
   *A61F 7/00*      (2006.01)

(56) References Cited

U.S. PATENT DOCUMENTS

| | | |
|---|---|---|
| 2,146,622 A | 2/1939 | Carlo |
| 2,148,661 A * | 2/1939 | Thierer .............. A61H 23/0254 |
| | | 219/521 |
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 2,954,898 A | 10/1960 | Feeberg |
| 3,261,042 A | 7/1966 | Baker |
| 3,320,682 A | 5/1967 | Sliman |
| 3,354,898 A | 11/1967 | Barnes |
| 3,559,640 A | 2/1971 | Beckett |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,871,381 A | 3/1975 | Roslonski |
| 3,901,225 A | 8/1975 | Sconce |
| 3,993,053 A | 11/1976 | Grossan |
| 4,020,209 A | 4/1977 | Yuan |
| 4,026,299 A | 5/1977 | Sauder |
| 4,116,476 A | 9/1978 | Porter et al. |
| 4,118,946 A | 10/1978 | Tubin |
| 4,147,921 A | 4/1979 | Walter et al. |
| 4,149,529 A | 4/1979 | Copeland et al. |
| 4,149,541 A | 4/1979 | Gammons et al. |
| 4,170,998 A | 10/1979 | Sauder |
| 4,184,537 A | 1/1980 | Sauder |
| 4,194,247 A | 3/1980 | Melander |
| 4,320,746 A | 3/1982 | Arkans et al. |
| 4,335,726 A | 6/1982 | Kolstedt |
| 4,338,944 A | 7/1982 | Arkans |
| D269,379 S | 6/1983 | Bledsoe |
| 4,407,276 A | 10/1983 | Bledsoe |
| 4,412,648 A | 11/1983 | Ford et al. |
| 4,436,125 A | 3/1984 | Blenkush |
| 4,441,504 A * | 4/1984 | Peterson ............ A61B 5/02233 |
| | | 600/490 |
| 4,460,085 A | 7/1984 | Jantzen |
| 4,463,751 A | 8/1984 | Bledsoe |
| 4,471,759 A | 9/1984 | Anderson et al. |
| 4,478,436 A | 10/1984 | Hashimoto |
| 4,547,906 A | 10/1985 | Nishida |
| 4,550,828 A | 11/1985 | Baldwin et al. |
| 4,597,384 A | 7/1986 | Whitney |
| 4,678,027 A | 7/1987 | Shirey et al. |
| 4,691,762 A | 9/1987 | Elkins et al. |
| 4,699,613 A | 10/1987 | Donawick et al. |
| 4,718,429 A | 1/1988 | Smidt |
| 4,738,119 A | 4/1988 | Zafred |
| 4,753,268 A | 6/1988 | Palau |
| 4,765,338 A | 8/1988 | Turner et al. |
| 4,817,588 A | 4/1989 | Bledsoe |
| 4,834,073 A | 5/1989 | Bledsoe et al. |
| 4,844,072 A | 7/1989 | French et al. |
| 4,884,304 A | 12/1989 | Elkins |
| 4,925,603 A | 5/1990 | Nambu |
| 4,955,369 A | 9/1990 | Bledsoe et al. |
| 4,955,435 A | 9/1990 | Shuster et al. |
| 4,962,761 A | 10/1990 | Golden |
| 4,964,282 A | 10/1990 | Wagner |
| 4,964,402 A | 10/1990 | Grim et al. |
| 4,966,145 A | 10/1990 | Kikumoto et al. |
| 4,976,262 A | 12/1990 | Palmacci |
| 5,002,270 A | 3/1991 | Shine |
| 5,014,695 A | 5/1991 | Benak et al. |
| 5,022,109 A | 6/1991 | Pekar |
| 5,033,136 A | 7/1991 | Elkins |
| 5,052,725 A | 10/1991 | Meyer et al. |
| 5,056,563 A | 10/1991 | Glossop |
| 5,072,875 A | 12/1991 | Zacoi |
| 5,074,285 A | 12/1991 | Wright |
| 5,076,068 A | 12/1991 | Mikhail |
| 5,080,089 A | 1/1992 | Mason et al. |
| 5,080,166 A | 1/1992 | Haugeneder |
| 5,086,771 A | 2/1992 | Molloy |
| 5,097,829 A | 3/1992 | Quisenberry |
| 5,104,158 A | 4/1992 | Meyer et al. |
| 5,112,045 A | 5/1992 | Mason et al. |
| 5,113,877 A | 5/1992 | Johnson, Jr. et al. |
| 5,163,425 A | 11/1992 | Nambu et al. |
| 5,163,923 A | 11/1992 | Donawick et al. |
| 5,172,689 A | 12/1992 | Wright |
| 5,186,698 A | 2/1993 | Mason et al. |
| 5,201,552 A | 4/1993 | Hohmann et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,269,369 A | 12/1993 | Faghri |
| D345,609 S | 3/1994 | Mason et al. |
| 5,294,156 A | 3/1994 | Kumazaki et al. |
| D345,802 S | 4/1994 | Mason et al. |
| D345,803 S | 4/1994 | Mason et al. |
| 5,303,716 A | 4/1994 | Mason et al. |
| 5,305,712 A | 4/1994 | Goldstein |
| 5,314,455 A | 5/1994 | Johnson, Jr. et al. |
| 5,316,250 A | 5/1994 | Mason et al. |
| 5,316,547 A | 5/1994 | Gildersleeve |
| D348,106 S | 6/1994 | Mason et al. |
| 5,324,319 A | 6/1994 | Mason et al. |
| D348,518 S | 7/1994 | Mason et al. |
| D351,472 S | 10/1994 | Mason et al. |
| 5,352,174 A | 10/1994 | Mason et al. |
| 5,353,605 A | 10/1994 | Naaman |
| 5,354,101 A | 10/1994 | Anderson, Jr. |
| 5,354,103 A | 10/1994 | Torrence et al. |
| D352,781 S | 11/1994 | Mason et al. |
| 5,372,575 A | 12/1994 | Sebastian |
| 5,383,689 A | 1/1995 | Wolfe, Sr. |
| 5,383,919 A | 1/1995 | Kelly et al. |
| RE34,883 E | 3/1995 | Grim |
| 5,395,399 A | 3/1995 | Rosenwald |
| 5,407,421 A | 4/1995 | Goldsmith |
| 5,411,541 A | 5/1995 | Bell et al. |
| 5,415,625 A | 5/1995 | Cassford et al. |
| 5,417,720 A | 5/1995 | Mason |
| 5,427,577 A | 6/1995 | Picchietti et al. |
| 5,441,533 A | 8/1995 | Johnson et al. |
| 5,449,379 A | 9/1995 | Hadtke |
| 5,451,201 A | 9/1995 | Prengler |
| 5,466,250 A | 11/1995 | Johnson, Jr. et al. |
| 5,468,220 A * | 11/1995 | Sucher ................ A61F 5/05866 |
| | | 2/170 |
| 5,470,353 A | 11/1995 | Jensen |
| 5,476,489 A | 12/1995 | Koewler |
| 5,484,448 A | 1/1996 | Steele et al. |
| 5,494,074 A | 2/1996 | Ramacier, Jr. et al. |
| 5,496,358 A | 3/1996 | Rosenwald |
| 5,507,792 A | 4/1996 | Mason et al. |
| 5,509,894 A | 4/1996 | Mason et al. |
| 5,514,081 A | 5/1996 | Mann |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| D372,534 S | 8/1996 | Andrews et al. |
| 5,553,712 A | 9/1996 | Tisbo et al. |
| 5,554,119 A | 9/1996 | Harrison et al. |
| 5,556,138 A | 9/1996 | Nakajima et al. |
| 5,564,124 A | 10/1996 | Elsherif et al. |
| 5,569,172 A | 10/1996 | Padden et al. |
| 5,592,694 A | 1/1997 | Yewer |
| 5,609,620 A | 3/1997 | Daily |
| 5,630,328 A | 5/1997 | Hise et al. |

(56) References Cited

U.S. PATENT DOCUMENTS

| | | | |
|---|---|---|---|
| 5,634,940 A | 6/1997 | Panyard | |
| 5,638,707 A | 6/1997 | Gould | |
| 5,645,671 A | 7/1997 | Tillinghast | |
| D382,113 S | 8/1997 | DuRapau | |
| D383,547 S | 9/1997 | Mason et al. | |
| D383,848 S | 9/1997 | Mason et al. | |
| 5,662,239 A | 9/1997 | Heuvelman | |
| 5,662,695 A | 9/1997 | Mason et al. | |
| 5,672,152 A | 9/1997 | Mason et al. | |
| 5,683,118 A | 11/1997 | Slocum | |
| 5,716,388 A | 2/1998 | Petelle | |
| 5,728,058 A | 3/1998 | Ouellette et al. | |
| 5,732,464 A | 3/1998 | Lamont | |
| 5,755,275 A | 5/1998 | Rose et al. | |
| 5,755,755 A | 5/1998 | Panyard | |
| 5,769,801 A | 6/1998 | Tumey et al. | |
| 5,772,618 A | 6/1998 | Mason et al. | |
| 5,782,780 A | 7/1998 | Mason et al. | |
| 5,792,216 A | 8/1998 | Kappel | |
| 5,807,294 A | 9/1998 | Cawley et al. | |
| 5,827,208 A | 10/1998 | Mason et al. | |
| 5,833,638 A | 11/1998 | Nelson | |
| 5,862,675 A | 1/1999 | Scaringe et al. | |
| 5,865,841 A | 2/1999 | Kolen et al. | |
| 5,866,219 A | 2/1999 | McClure et al. | |
| 5,868,690 A | 2/1999 | Eischen, Sr. | |
| 5,871,526 A | 2/1999 | Gibbs et al. | |
| 5,895,418 A | 4/1999 | Saringer | |
| 5,913,885 A | 6/1999 | Klatz et al. | |
| 5,920,934 A | 7/1999 | Hannagan et al. | |
| 5,951,598 A | 9/1999 | Bishay et al. | |
| 5,967,225 A | 10/1999 | Jenkins | |
| 5,968,072 A | 10/1999 | Hite et al. | |
| 5,970,519 A | 10/1999 | Weber | |
| 5,980,561 A | 11/1999 | Kolen et al. | |
| 5,984,885 A | 11/1999 | Gaylord, Jr. et al. | |
| 5,989,285 A | 11/1999 | DeVilbiss et al. | |
| 5,992,459 A | 11/1999 | Sugita et al. | |
| 5,997,495 A | 12/1999 | Cook et al. | |
| 6,030,412 A | 2/2000 | Klatz et al. | |
| 6,036,107 A | 3/2000 | Aspen et al. | |
| 6,036,718 A | 3/2000 | Ledford et al. | |
| 6,048,326 A | 4/2000 | Davis et al. | |
| 6,053,169 A | 4/2000 | Hunt | |
| 6,055,670 A | 5/2000 | Parker | |
| 6,058,508 A | 5/2000 | Brown Honeysuckle | |
| 6,074,413 A | 6/2000 | Davis et al. | |
| 6,083,256 A | 7/2000 | Der Ovanesian | |
| 6,089,593 A | 7/2000 | Hanson et al. | |
| D430,288 S | 8/2000 | Mason et al. | |
| D430,289 S | 8/2000 | Mason et al. | |
| 6,105,382 A | 8/2000 | Reason | |
| 6,109,338 A | 8/2000 | Butzer | |
| 6,117,164 A | 9/2000 | Gildersleeve et al. | |
| 6,146,347 A * | 11/2000 | Porrata | A61F 5/0118 |
| | | | 128/879 |
| 6,146,413 A | 11/2000 | Harman | |
| 6,156,059 A | 12/2000 | Olofsson | |
| 6,178,562 B1 | 1/2001 | Elkins | |
| 6,228,106 B1 | 5/2001 | Simbruner et al. | |
| 6,238,427 B1 | 5/2001 | Matta | |
| 6,254,554 B1 | 7/2001 | Turtzo | |
| 6,260,890 B1 | 7/2001 | Mason | |
| 6,261,314 B1 | 7/2001 | Rich | |
| 6,270,481 B1 | 8/2001 | Mason et al. | |
| 6,306,112 B2 | 10/2001 | Bird | |
| 6,328,276 B1 | 12/2001 | Falch et al. | |
| 6,349,412 B1 | 2/2002 | Dean | |
| 6,352,550 B1 | 3/2002 | Gildersleeve et al. | |
| 6,354,635 B1 | 3/2002 | Dyson et al. | |
| 6,361,514 B1 | 3/2002 | Brown et al. | |
| 6,368,357 B1 | 4/2002 | Schon et al. | |
| 6,371,976 B1 | 4/2002 | Vrzalik et al. | |
| 6,382,678 B1 | 5/2002 | Field et al. | |
| 6,398,748 B1 | 6/2002 | Wilson | |
| 6,405,080 B1 | 6/2002 | Lasersohn et al. | |
| 6,406,445 B1 | 6/2002 | Ben-nun | |
| 6,440,159 B1 | 8/2002 | Edwards et al. | |
| 6,443,498 B1 | 9/2002 | Liao | |
| 6,508,831 B1 | 1/2003 | Kushnir | |
| 6,547,284 B2 | 4/2003 | Rose et al. | |
| 6,551,264 B1 | 4/2003 | Cawley et al. | |
| 6,551,347 B1 | 4/2003 | Elkins | |
| 6,551,348 B1 | 4/2003 | Blalock et al. | |
| 6,620,187 B2 | 9/2003 | Carson et al. | |
| 6,641,601 B1 | 11/2003 | Augustine et al. | |
| 6,645,232 B2 | 11/2003 | Carson | |
| 6,660,027 B2 | 12/2003 | Gruszecki et al. | |
| D486,870 S | 2/2004 | Mason | |
| 6,695,872 B2 | 2/2004 | Elkins | |
| 6,699,267 B2 | 3/2004 | Voorhees et al. | |
| 6,719,713 B2 | 4/2004 | Mason | |
| 6,719,728 B2 | 4/2004 | Mason et al. | |
| 6,802,823 B2 | 10/2004 | Mason | |
| 6,818,012 B2 | 11/2004 | Ellingboe | |
| 6,823,682 B1 | 11/2004 | Jenkins et al. | |
| 6,871,878 B2 | 3/2005 | Miros | |
| 6,893,414 B2 | 5/2005 | Goble et al. | |
| 6,926,311 B2 | 8/2005 | Chang et al. | |
| 6,932,304 B1 | 8/2005 | Villamar | |
| 6,936,019 B2 | 8/2005 | Mason | |
| 6,942,015 B1 | 9/2005 | Jenkins | |
| 6,948,501 B2 * | 9/2005 | Rastegar | A61H 9/0078 |
| | | | 128/845 |
| 7,008,445 B2 | 3/2006 | Lennox | |
| 7,017,213 B2 | 3/2006 | Chisari | |
| 7,025,709 B2 | 4/2006 | Riggall | |
| 7,059,329 B2 | 6/2006 | Mason et al. | |
| 7,060,045 B2 | 6/2006 | Mason et al. | |
| 7,060,086 B2 | 6/2006 | Wilson et al. | |
| 7,093,903 B2 | 8/2006 | O'Connor et al. | |
| 7,107,629 B2 | 9/2006 | Miros et al. | |
| 7,108,664 B2 | 9/2006 | Mason et al. | |
| 7,117,569 B2 | 10/2006 | Bledsoe | |
| 7,125,417 B2 | 10/2006 | Mizrahi | |
| 7,141,131 B2 | 11/2006 | Foxen et al. | |
| 7,156,054 B1 | 1/2007 | York | |
| 7,166,083 B2 | 1/2007 | Bledsoe | |
| 7,191,798 B2 | 3/2007 | Edelman et al. | |
| 7,198,093 B1 | 4/2007 | Elkins | |
| 7,235,059 B2 | 6/2007 | Mason et al. | |
| 7,244,239 B2 | 7/2007 | Howard | |
| 7,306,568 B2 | 12/2007 | Diana | |
| 7,308,304 B2 | 12/2007 | Hampton et al. | |
| 7,326,196 B2 | 2/2008 | Olsen et al. | |
| 7,418,755 B2 | 9/2008 | Bledsoe et al. | |
| 7,434,844 B2 | 10/2008 | Kao | |
| 7,448,653 B2 | 11/2008 | Jensen et al. | |
| 7,479,122 B2 | 1/2009 | Ceriani et al. | |
| 7,485,103 B2 | 2/2009 | Mason et al. | |
| 7,490,620 B2 | 2/2009 | Tesluk et al. | |
| 7,500,957 B2 | 3/2009 | Bledsoe | |
| 7,640,764 B2 | 1/2010 | Gammons et al. | |
| 7,658,205 B1 | 2/2010 | Edelman et al. | |
| 7,694,693 B1 | 4/2010 | Edelman et al. | |
| 7,731,244 B2 | 6/2010 | Miros et al. | |
| 7,785,283 B1 | 8/2010 | Bledsoe | |
| 7,833,184 B2 * | 11/2010 | Chiodo | A61F 5/0111 |
| | | | 128/882 |
| 7,837,638 B2 | 11/2010 | Miros et al. | |
| 7,864,941 B1 | 1/2011 | Bledsoe et al. | |
| 7,871,427 B2 | 1/2011 | Dunbar et al. | |
| 7,896,910 B2 | 3/2011 | Schirrmacher et al. | |
| 7,908,692 B2 | 3/2011 | Lange | |
| 7,914,563 B2 | 3/2011 | Mason et al. | |
| 7,959,588 B1 | 6/2011 | Wolpa | |
| 7,988,653 B2 | 8/2011 | Fout et al. | |
| 8,016,779 B2 | 9/2011 | Brown et al. | |
| 8,052,628 B1 | 11/2011 | Edelman et al. | |
| 8,066,752 B2 | 11/2011 | Hamilton et al. | |
| 8,109,273 B2 | 2/2012 | Golden et al. | |
| 8,182,521 B2 | 5/2012 | Kane et al. | |
| 8,216,163 B2 | 7/2012 | Edelman | |
| 8,216,290 B2 | 7/2012 | Shawver et al. | |

(56) References Cited

U.S. PATENT DOCUMENTS

| | | |
|---|---|---|
| 8,216,398 B2 | 7/2012 | Bledsoe et al. |
| 8,226,698 B2 | 7/2012 | Edelman et al. |
| 8,251,932 B2 | 8/2012 | Fout |
| 8,251,936 B2 | 8/2012 | Fout et al. |
| 8,273,045 B2 | 9/2012 | Ceriani |
| 8,277,403 B2 | 10/2012 | Ceriani et al. |
| 8,328,742 B2 | 12/2012 | Bledsoe |
| 8,414,512 B2 | 4/2013 | Fout |
| 8,419,670 B2 | 4/2013 | Downing |
| 8,425,579 B1 | 4/2013 | Edelman et al. |
| 8,444,581 B1 | 5/2013 | Maxon-Maldonado et al. |
| 8,512,263 B2 | 8/2013 | Gammons |
| 8,597,217 B2 | 12/2013 | Lowe et al. |
| 8,613,762 B2 | 12/2013 | Bledsoe |
| 8,715,330 B2 | 5/2014 | Lowe et al. |
| 9,132,057 B2 | 9/2015 | Wilford et al. |
| 2001/0018604 A1 | 8/2001 | Elkins |
| 2001/0034545 A1 | 10/2001 | Elkins |
| 2001/0034546 A1 | 10/2001 | Elkins |
| 2001/0039439 A1 | 11/2001 | Elkins et al. |
| 2002/0019657 A1 | 2/2002 | Elkins |
| 2002/0026226 A1 | 2/2002 | Ein |
| 2002/0032473 A1 | 3/2002 | Kushnir et al. |
| 2002/0041621 A1 | 4/2002 | Faries et al. |
| 2002/0058975 A1 | 5/2002 | Bieberich |
| 2002/0082668 A1 | 6/2002 | Ingman |
| 2002/0093189 A1 | 7/2002 | Krupa |
| 2002/0108279 A1 | 8/2002 | Hubbard et al. |
| 2003/0060761 A1 | 3/2003 | Evans et al. |
| 2003/0196352 A1 | 10/2003 | Bledsoe et al. |
| 2004/0064170 A1 | 4/2004 | Radons et al. |
| 2004/0064171 A1 | 4/2004 | Briscoe et al. |
| 2004/0068309 A1 | 4/2004 | Edelman |
| 2004/0158303 A1 | 8/2004 | Lennox et al. |
| 2004/0167594 A1 | 8/2004 | Elkins |
| 2004/0210283 A1 | 10/2004 | Rose et al. |
| 2004/0225341 A1 | 11/2004 | Schock et al. |
| 2004/0243202 A1 | 12/2004 | Lennox |
| 2005/0027173 A1 | 2/2005 | Briscoe et al. |
| 2005/0065581 A1 | 3/2005 | Fletcher et al. |
| 2005/0126578 A1 | 6/2005 | Garrison et al. |
| 2005/0131324 A1 | 6/2005 | Bledsoe |
| 2005/0136213 A1 | 6/2005 | Seth et al. |
| 2005/0143796 A1 | 6/2005 | Augustine et al. |
| 2005/0143797 A1 | 6/2005 | Parish et al. |
| 2006/0058858 A1 | 3/2006 | Smith |
| 2006/0069418 A1 | 3/2006 | Schock et al. |
| 2006/0144557 A1 | 7/2006 | Koscheyev et al. |
| 2006/0190062 A1 | 8/2006 | Worthen |
| 2006/0200057 A1 | 9/2006 | Sterling |
| 2006/0287697 A1 | 12/2006 | Lennox |
| 2007/0060987 A1 | 3/2007 | Grahn et al. |
| 2007/0068651 A1 | 3/2007 | Gammons et al. |
| 2007/0108829 A1 | 5/2007 | Lehn et al. |
| 2007/0118194 A1 | 5/2007 | Mason et al. |
| 2007/0118965 A1 | 5/2007 | Hoffman |
| 2007/0157931 A1 | 7/2007 | Parker et al. |
| 2007/0161932 A1 | 7/2007 | Pick et al. |
| 2007/0161933 A1 | 7/2007 | Ravikumar |
| 2007/0167895 A1 | 7/2007 | Gramza et al. |
| 2007/0191918 A1 | 8/2007 | MacHold et al. |
| 2007/0282230 A1 | 12/2007 | Valderrabano et al. |
| 2008/0000474 A1 | 1/2008 | Jochle et al. |
| 2008/0058911 A1 | 3/2008 | Parish et al. |
| 2008/0065172 A1 | 3/2008 | Magdych |
| 2008/0067095 A1 | 3/2008 | Mueller |
| 2008/0097560 A1 | 4/2008 | Radziunas et al. |
| 2008/0097561 A1 | 4/2008 | Melsky et al. |
| 2008/0132816 A1* | 6/2008 | Kane .................. A61H 7/001 601/152 |
| 2008/0132976 A1 | 6/2008 | Kane et al. |
| 2008/0161891 A1 | 7/2008 | Pierre et al. |
| 2008/0234788 A1 | 9/2008 | Wasowski |
| 2008/0249593 A1 | 10/2008 | Cazzini et al. |
| 2008/0269852 A1 | 10/2008 | Lennox et al. |
| 2008/0275534 A1 | 11/2008 | Noel |
| 2008/0283426 A1 | 11/2008 | Primer et al. |
| 2009/0005841 A1 | 1/2009 | Schirrmacher et al. |
| 2009/0018623 A1 | 1/2009 | Levinson et al. |
| 2009/0038195 A1 | 2/2009 | Riker et al. |
| 2009/0062890 A1 | 3/2009 | Ugajin et al. |
| 2009/0069731 A1 | 3/2009 | Parish et al. |
| 2009/0183410 A1 | 7/2009 | Tursso et al. |
| 2010/0006631 A1 | 1/2010 | Edwards et al. |
| 2010/0076531 A1 | 3/2010 | Beran et al. |
| 2010/0089896 A1 | 4/2010 | Bart |
| 2010/0094187 A1 | 4/2010 | Murinson et al. |
| 2010/0137951 A1 | 6/2010 | Lennox et al. |
| 2010/0137953 A1 | 6/2010 | Stein |
| 2010/0139294 A1 | 6/2010 | Lowe et al. |
| 2010/0145421 A1 | 6/2010 | Tomlinson et al. |
| 2010/0161013 A1 | 6/2010 | Heaton |
| 2010/0217349 A1 | 8/2010 | Fahey |
| 2010/0241120 A1 | 9/2010 | Bledsoe et al. |
| 2011/0004132 A1 | 1/2011 | Cook |
| 2011/0028873 A1 | 2/2011 | Miros et al. |
| 2011/0040359 A1 | 2/2011 | Harris et al. |
| 2011/0046700 A1 | 2/2011 | McDonald et al. |
| 2011/0087142 A1 | 4/2011 | Ravikumar et al. |
| 2011/0098792 A1* | 4/2011 | Lowe .................. A61F 7/02 607/104 |
| 2011/0106023 A1 | 5/2011 | Lowe |
| 2011/0152982 A1 | 6/2011 | Richardson |
| 2011/0152983 A1 | 6/2011 | Schirrmacher et al. |
| 2011/0172749 A1 | 7/2011 | Christensen et al. |
| 2011/0307038 A1 | 12/2011 | Stiehr et al. |
| 2012/0010546 A1 | 1/2012 | Sotereanos et al. |
| 2012/0028764 A1* | 2/2012 | Miller .............. A63B 21/00189 482/44 |
| 2012/0143111 A1 | 6/2012 | Bledsoe et al. |
| 2012/0172774 A1* | 7/2012 | Lowe .................. A61F 7/02 602/13 |
| 2012/0172955 A1 | 7/2012 | Dewaegenaere |
| 2012/0179084 A1 | 7/2012 | Lipshaw et al. |
| 2012/0233736 A1 | 9/2012 | Tepper et al. |
| 2012/0245483 A1 | 9/2012 | Lundqvist |
| 2012/0288848 A1 | 11/2012 | Latham et al. |
| 2012/0330199 A1 | 12/2012 | Lurie et al. |
| 2012/0330202 A1 | 12/2012 | Flick |
| 2013/0006154 A1 | 1/2013 | Lowe |
| 2013/0012847 A1 | 1/2013 | Lowe et al. |
| 2013/0013033 A1 | 1/2013 | Lowe |
| 2013/0090683 A1 | 4/2013 | Schock |
| 2013/0123890 A1 | 5/2013 | Latham |
| 2013/0165847 A1 | 6/2013 | Scarpaci et al. |
| 2013/0190553 A1 | 7/2013 | Wong et al. |
| 2013/0245519 A1 | 9/2013 | Edelman et al. |
| 2013/0245729 A1 | 9/2013 | Edelman et al. |
| 2013/0296981 A1 | 11/2013 | Saggers |
| 2014/0074198 A1 | 3/2014 | Bledsoe |
| 2014/0078086 A1 | 3/2014 | Bledsoe et al. |
| 2014/0142473 A1 | 5/2014 | Lowe et al. |
| 2014/0222121 A1 | 8/2014 | Spence et al. |
| 2014/0236256 A1 | 8/2014 | Rossing |
| 2014/0243939 A1 | 8/2014 | Lowe et al. |
| 2014/0277301 A1* | 9/2014 | Varga .................. A61F 7/02 607/104 |
| 2014/0316314 A1 | 10/2014 | Schubert |
| 2015/0224015 A1 | 8/2015 | Wilford et al. |
| 2015/0320588 A1 | 11/2015 | Connor |
| 2015/0335468 A1 | 11/2015 | Rose et al. |
| 2015/0374538 A1 | 12/2015 | Rogers |
| 2016/0030234 A1 | 2/2016 | Lofy et al. |
| 2016/0128865 A1 | 5/2016 | Lowe |
| 2016/0166428 A1 | 6/2016 | Hilton et al. |
| 2018/0207025 A1 | 7/2018 | Lowe et al. |
| 2018/0271688 A1 | 9/2018 | Miros et al. |

FOREIGN PATENT DOCUMENTS

| | | |
|---|---|---|
| CN | 2880025 Y | 3/2007 |
| CN | 201001805 Y | 1/2008 |
| CN | 201070419 Y | 6/2008 |

(56) References Cited

FOREIGN PATENT DOCUMENTS

| | | |
|---|---|---|
| CN | 101524301 A | 9/2009 |
| DE | 3343664 | 3/1985 |
| DE | 29716336 U1 | 1/1998 |
| DE | 29716338 U1 | 1/1998 |
| EP | 0344949 A2 | 12/1989 |
| EP | 0412708 A1 | 2/1991 |
| EP | 0535830 A1 | 4/1993 |
| EP | 0861651 B1 | 4/2002 |
| EP | 1329676 A1 | 7/2003 |
| EP | 1393751 A1 | 3/2004 |
| EP | 1972312 A2 | 9/2008 |
| FR | 819022 | 10/1937 |
| IT | 330552 | 10/1935 |
| JP | 08-229061 A | 9/1996 |
| JP | 2000288007 A | 10/2000 |
| KR | 20-0153967 | 8/1999 |
| KR | 100654317 B1 | 12/2006 |
| NL | 2011288 C | 8/2013 |
| WO | WO92/13506 A1 | 8/1992 |
| WO | WO92/15263 A1 | 9/1992 |
| WO | WO94/09732 A1 | 5/1994 |
| WO | WO96/26693 A1 | 9/1996 |
| WO | WO98/07397 A1 | 2/1998 |
| WO | WO99/44552 A1 | 9/1999 |
| WO | WO00/23016 A1 | 4/2000 |
| WO | WO00/55542 A1 | 9/2000 |
| WO | WO00/67685 A1 | 11/2000 |
| WO | WO02/19954 A2 | 3/2002 |
| WO | WO02/38091 A1 | 5/2002 |
| WO | WO 03/000079 A2 | 1/2003 |
| WO | WO03/072008 A2 | 9/2003 |
| WO | WO2005/007060 A2 | 1/2005 |
| WO | WO2005/082301 A1 | 9/2005 |
| WO | WO2006/110405 A2 | 10/2006 |
| WO | WO2010/060931 A1 | 6/2010 |
| WO | WO2011/019603 A1 | 2/2011 |

OTHER PUBLICATIONS

Lowe, U.S. Appl. No. 13/441,770 entitled "Thermal Therapy System," filed Apr. 6, 2012.

BioCompression Systems, Inc. (Moonachie, NJ); Product literature for Sequential Circulators; 15 pgs.; Oct. 1997.

Van Eps et al.; distal limb cryotherapy for the prevention of acute laminitis; Clin Tech Equine Pract; vol. 3; pp. 64-70; Mar. 2004.

Van Eps et al.; Equine laminitis: cryotherapy reduces the severity of the acute lesion; Equine Veterinary Journal; vol. 36; No. 3; pp. 255-260; Apr. 2004.

Schirrmacher et al.; U.S. Appl. No. 14/819,276 entitled "Integrated multisectional heat exchanger," filed Aug. 5, 2015.

Webster Dictionary; Shunt (definition); Merriam-Webster, Inc.; 11 pages; retrieved from the internet (https://www.merriam-webster.com/dictionary/shunt on Apr. 13, 2018.

Lowe et al.; U.S. Appl. No. 15/483,980 entitled "Reinforced therapeutic wrap and method," filed Apr. 10, 2017.

Hilton et al., U.S. Appl. No. 16/178,467 entitled "Integrated multisectional heat exchanger," filed Nov. 1, 2018.

Johns Hopkins Medicine; Patient guide to UCL injuries of the elbow (ulnar collateral ligament); 8 pages; Sep. 3, 2010; retrieved from the internet Apr. 20, 2015 (http:/www.hopkinsortho.org/ucl.html).

\* cited by examiner

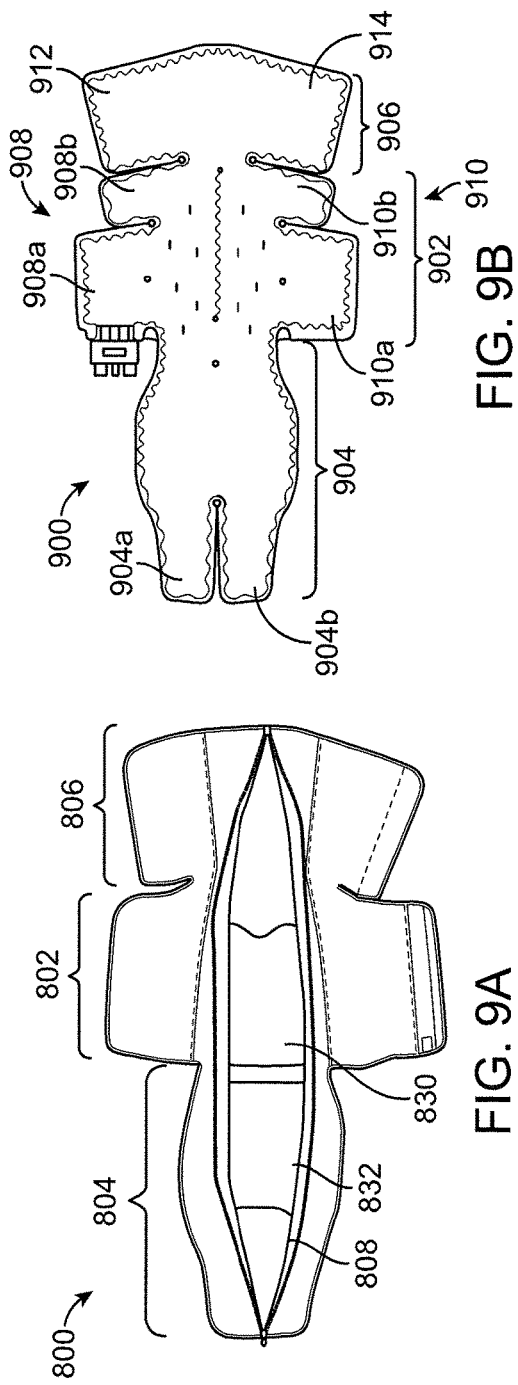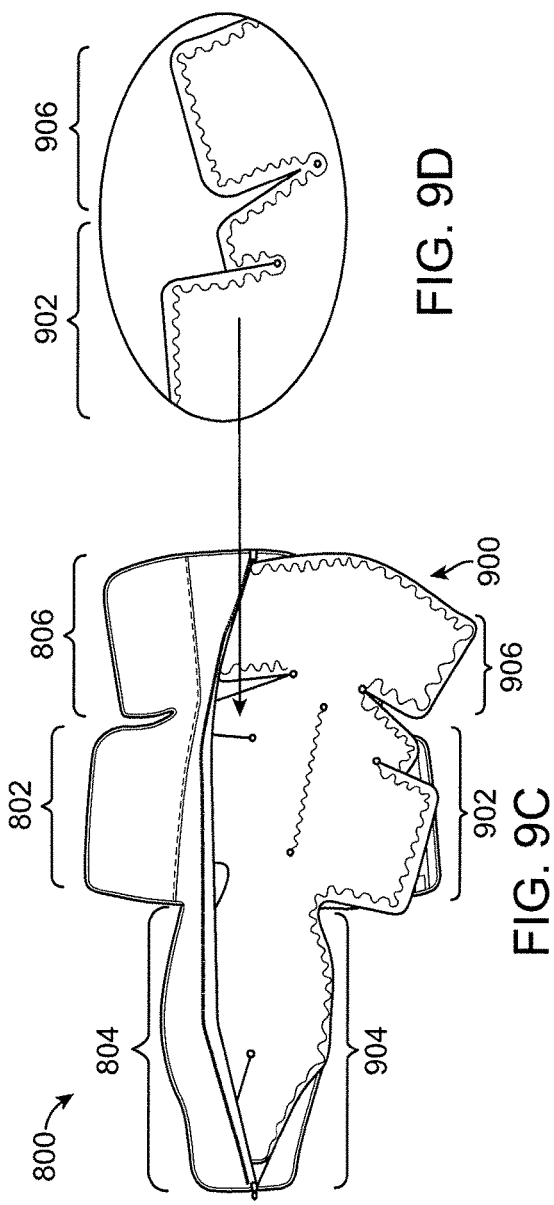

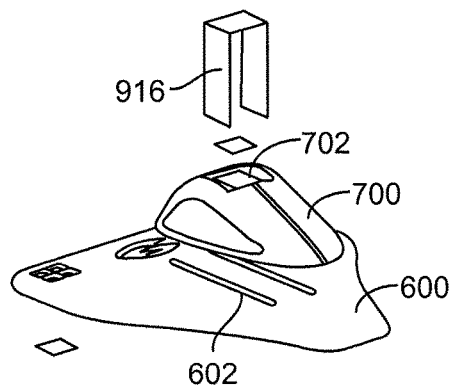
FIG. 9E
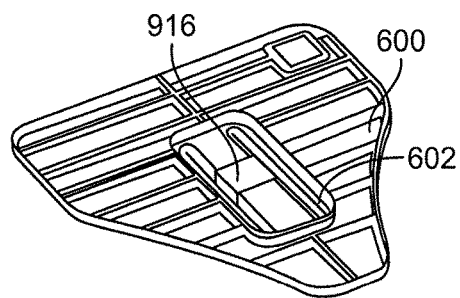
FIG. 9F
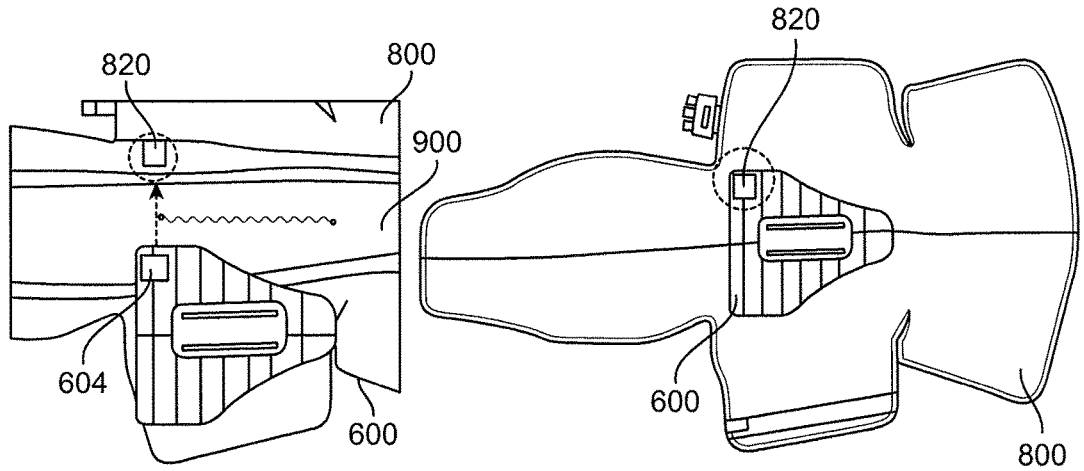
FIG. 9G
FIG. 9H
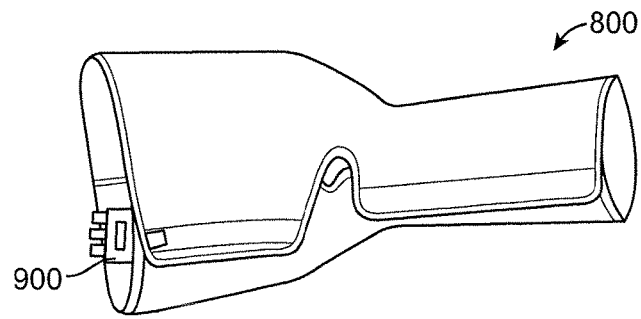
FIG. 9I

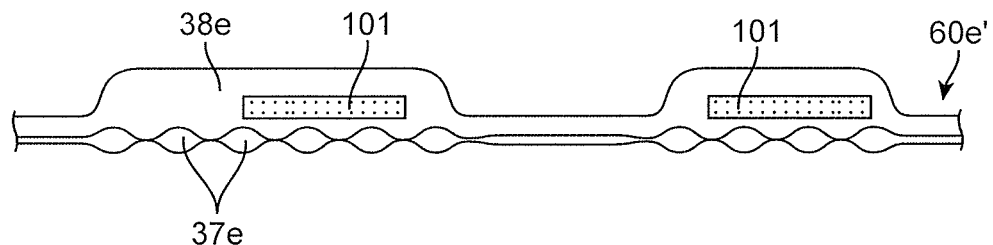
FIG. 10A
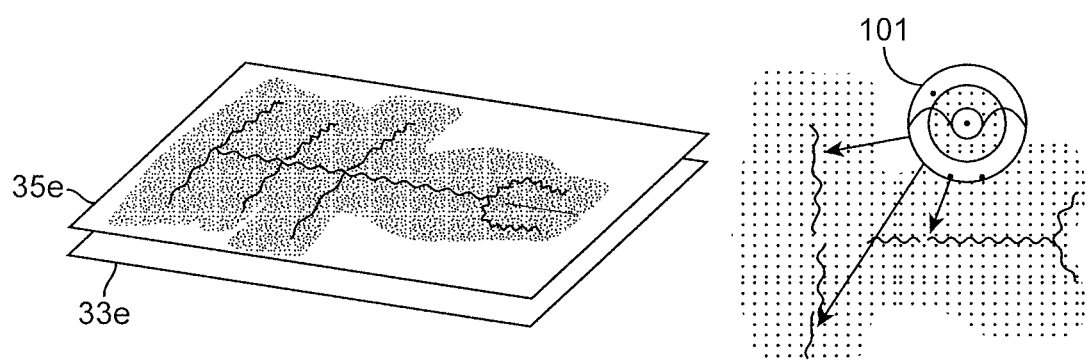
FIG. 10B
FIG. 10C
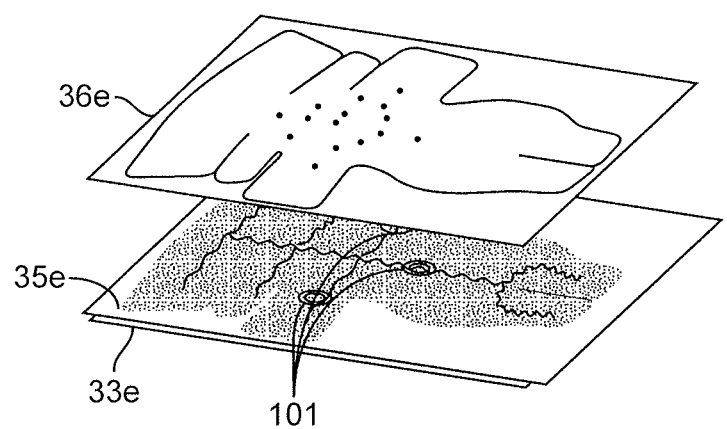
FIG. 10D

HAND AND FOOT WRAPS

CROSS REFERENCE TO RELATED APPLICATIONS

This application claims priority to U.S. Provisional Patent Application No. 61/885,440, filed Oct. 1, 2013 and titled "HAND WRAP," which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to therapy wraps. More specifically, embodiments of the invention relate to wraps for the hand, wrist, and/or forearm that provide thermal and compression therapy.

BACKGROUND

It is known to provide temperature-controlled, compressive, and/or other therapy to the body. For example, temperature-controlled therapy has long been practiced for physical therapy, sports injuries, and other settings. Thermal therapy commonly includes cooling, heating, and/or applying compression to a traumatized area of a human body to facilitate healing and prevent unwanted consequences of the trauma. This form of therapy is commonly referred to as RICE (Rest, Ice, Compression and Elevation). RICE is also commonly used in sports medicine to reduce the risk of long-term damage to muscles and joints and/or alleviate pain and soreness.

There has been a focus with existing therapy wrap designs on improving conformance to body parts. Better conformance generally leads to improved therapy and the ability to use therapy wraps in a greater array of applications. Conventional therapy devices generally suffer from poor conformance to complex portions of the patient's anatomy, such as the patient's hand.

There is a need for thermal therapy wraps with better conformance properties. There is the need for therapy wraps that can be applied to a specific type of anatomical shape, such as the hand. There is a need for a therapy wrap that achieves better apposition of a therapy component to the body. There is a need for improved systems and methods for heating, cooling, and/or compressing a body in need of treatment.

These and other problems are overcome by the invention disclosed herein.

SUMMARY OF THE DISCLOSURE

The present invention involves improvements in therapy apparatus and avoids disadvantages in the prior art.

Various aspects of the invention are directed to a device for providing treatment to a body part, the device comprising a therapy component for applying thermal therapy, compression therapy, or both; a sleeve for receiving the therapy device and sized and shaped to cover a patient's hand.

In some embodiments, a therapy wrap for treating a hand of a patient is provided. The therapy wrap can include a sleeve comprising a palm facing portion and a hand covering portion; a hand support disposed within the palm facing portion of the sleeve, the hand support having a convex, curved palm facing surface configured to conform to a shape of the patient's hand in a relaxed state; and a therapy component comprising a heat exchanger disposed in both the palm facing portion and the hand covering portion of the sleeve, the heat exchanger comprising a compliant fluid bladder.

In some embodiments, the hand support is secured to a base plate.

In some embodiments, the base plate is configured to resist circumferential compression.

In some embodiments, the base plate is made of a rigid material.

In some embodiments, the hand support is made of a resilient material.

In some embodiments, the hand support is made of a rigid material.

In some embodiments, the resilient material is selected from the group consisting of a foam and a gel.

In some embodiments, the base plate comprises a slot configured to receive the therapy component.

In some embodiments, the base plate further comprises a retaining member with a curved surface that forms the slot with the base plate.

In some embodiments, a portion of the therapy component is disposed through the slot and wrapped around the cylindrical retaining member when the therapy component is in a folded configuration.

In some embodiments, the hand support is slidably secured to the base plate.

In some embodiments, the hand support is removably secured to the base plate.

In some embodiments, the base plate is attached to the palm facing portion of the sleeve.

In some embodiments, the therapy component further comprises an air bladder.

In some embodiments, the air bladder is positioned on an outer portion of the therapy component and the heat exchanger is positioned on an inner portion of the therapy component, wherein the inner portion of the therapy component is configured to face the patient's hand.

In some embodiments, the air bladder comprises one or more reinforcement members located along portions of the air bladder that are configured to fold.

In some embodiments, the one or more reinforcement members are made of foam.

In some embodiments, the sleeve further comprises a forearm wrap portion.

In some embodiments, the therapy component extends into the forearm wrap portion.

In some embodiments, the therapy component further comprises an air bladder, wherein the air bladder provides is configured to provide circumferential compression in the forearm wrap portion.

In some embodiments, the hand support is secured to a base plate that is configured to resist circumferential compression.

In some embodiments, the base plate extends into the forearm wrap portion.

In some embodiments, the palm facing portion has a first pair of wings and the forearm wrap portion has a second pair of wings.

In some embodiments, the therapy wrap further includes a thermal insulating member disposed in a portion of the palm facing portion of the sleeve.

In some embodiments, the thermal insulating member extends into the hand covering portion of the sleeve.

In some embodiments, the therapy wrap further includes a second thermal insulating member disposed in the hand covering portion of the sleeve.

In some embodiments, the thermal insulating member is removably attached to the sleeve.

In some embodiments, the thermal insulting member is attached within the sleeve to divide the palm facing portion into a skin facing compartment and an outer compartment, wherein both the skin facing compartment and the outer compartment are configured to removably receive the therapy wrap.

In some embodiments, a method for treating a hand of a patient is provided. The method can include wrapping a hand of the patient with a sleeve such that the patient's palm is facing a palm facing portion of the sleeve and the back of the patient's hand is facing a hand covering portion of the sleeve; conforming the patient's hand in a relaxed state to a hand support disposed within the palm facing portion of the sleeve, the hand support having a convex, curved palm facing surface; and circulating a heat exchange fluid through a therapy component comprising a heat exchanger disposed in both the palm facing portion and the hand covering portion of the sleeve.

In some embodiments, the method further includes applying a flat pressure to the palm and the back of the patient's hand by inflating an air bladder that forms a part of the therapy component.

In some embodiments, the method further includes resisting circumferential compression of the patient's hand by securing the hand support to a rigid base plate.

In some embodiments, the method further includes wrapping the patient's forearm with a forearm portion of the sleeve.

In some embodiments, the method further includes applying a circumferential pressure to the patient's forearm.

In some embodiments, the method further includes positioning a thermal insulating member between the patient's fingers and the therapy component.

In some embodiments, the thermal insulating member is removably placed.

In some embodiments, a therapy wrap for treating an extremity of a patient is provided. The therapy wrap can include a sleeve comprising a palmar or plantar aspect facing portion and a dorsal aspect covering portion; a rigid base plate removably disposed in the palmar or plantar aspect facing portion of the sleeve, wherein the rigid base plate is configured to resist circumferential pressure; and a therapy component comprising a heat exchanger disposed in both the palmar or plantar aspect facing portion and the dorsal aspect covering portion of the sleeve, the heat exchanger comprising a compliant fluid bladder.

In some embodiments, the sleeve further comprises a forelimb wrap portion.

In some embodiments, the base plate comprises a palmar or plantar aspect facing side and an opposing side opposite the palmar or plantar aspect facing side, wherein an attachment feature is disposed on the opposing side, the attachment feature configured to removably attach to a complementary attachment feature on an inner surface of the palmar or plantar aspect facing portion of the sleeve.

In some embodiments, the therapy wrap further includes a first thermal insulating member disposed in the palmar or plantar aspect facing portion and a second thermal insulating member disposed in the dorsal aspect covering portion of the sleeve.

In some embodiments, the first thermal insulating member is attached within the sleeve to divide the palmar or plantar aspect facing portion into a skin facing compartment and an outer compartment, and the second thermal insulating member is attached within the sleeve to divide the dorsal aspect covering portion into a skin facing compartment and an outer compartment, wherein all the skin facing compartments and the outer compartments are configured to removably receive the therapy wrap.

In some embodiments, the therapy component further comprises an air bladder, wherein the air bladder is positioned on an outer portion of the therapy component and the heat exchanger is positioned on an inner portion of the therapy component, wherein the inner portion of the therapy component is configured to face the patient's palmar or plantar aspect.

In some embodiments, the air bladder comprises one or more reinforcement members located along portions of the air bladder that are configured to fold.

In some embodiments, the one or more reinforcement members are made of foam.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9I illustrate the assembly of an embodiment of a therapy wrap from the components illustrated in FIGS. 6A-8D along with an embodiment of a therapy component.

FIGS. 10A-10F illustrate various embodiments of a reinforcement member that can be disposed within a gas pressure bladder to prevent or reduce kinking in the gas bladder.

DETAILED DESCRIPTION

Figure 1A:
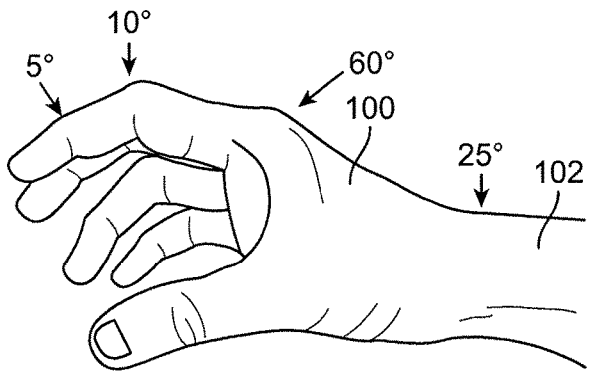
FIG. 1A is an illustration of a hand in a natural, relaxed, and unstressed configuration.
Figure 1B:
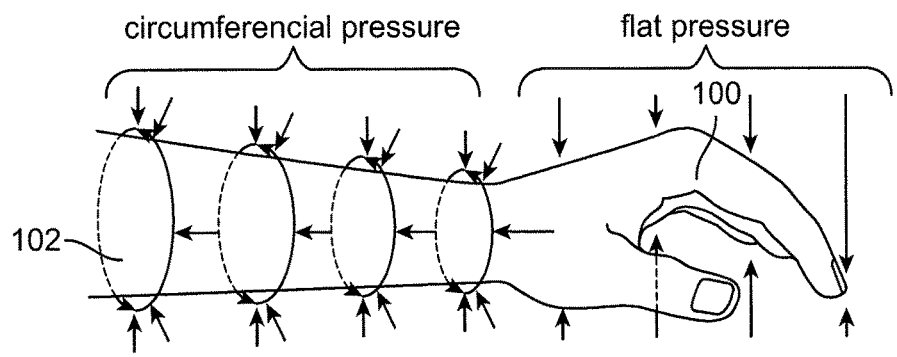
FIG. 1B shows two zone compression of the patient's forearm and hand, with circumferential pressure applied to the forearm and flat pressure applied to the hand.

FIG. 1A shows a patient's hand 100 in a natural, relaxed, and unstressed configuration. As shown, the hand 100 is not flat, nor are the fingers compressed together. Instead, the fingers are curved and separated from each other so that they are not overlapping. FIG. 1B illustrates that in some embodiments, it may be desirable to provide two zone compression, such that the patient's hand 100 receives a generally flat pressure from above and below the hand, while the forearm 102 receives a generally circumferential pressure that applies force normal to the surface of the skin. By applying a flat pressure instead of a circumferential pressure to the patient's hand, the fingers and palm of the patient's hand are not forced into a stressed, compressed, cylindrical configuration, and instead, is directed to a flat configuration. To resist compression of the hand into a flat configuration, a hand support can be used as further described below. Application of a flat pressure to the hand in combination with a hand support can maintain the hand in a more natural, relaxed, and unstressed configuration during the thermal and compressive treatment process.

FIGS. 2A-2D illustrate a therapy wrap 200 that is specifically designed to be used on a patient's hand 100 and forearm 102. The therapy wrap 200 can comprise an outer sleeve 202 that reversibly or removably receives a therapy component 204. The therapy component 204 can include a heat exchanger 206, such as a fluid bladder or chamber, and a compressive element 208, such as an air bladder or chamber. The compressive element may also be the fluid bladder itself. Various elements of the therapy wrap 200 are described below.

The device may be configured for administering temperature-controlled therapy to a body including, but not limited to, the application of cooling, heating, and/or compression. Specifically, the exemplary therapy component is a thermal therapy device including a heat exchanger to exchange heat with the body part and a compressive mechanism for applying a compressive force to the body part.

The heat exchanger may be a compliant fluid bladder for circulating a heat transfer medium. The compressive mechanism may be a compliant gas pressure bladder that overlays the fluid bladder. The gas pressure bladder directs a compressive force to the fluid bladder to press the bladder against the body part to be subjected to heat exchange and apply compression to the body part. Compression therapy is commonly used to reduce edema. It is commonly used in conjunction with heating or cooling therapy.

Various aspects of the therapy device may be similar to the devices disclosed by U.S. Pat. No. 7,107,629 to Miros et al. and U.S. Patent Pub. No. 2005/0256556 A1 to Schirrmacher et al., the entire contents of which are incorporated herein for all purposes by reference. The fluid bladder is adapted exchange heat with an adjacent body when the fluid is circulated in the bladder. The body may include, but is not limited to, a mammalian body such as a human or an equine animal. Various aspects of the use of the exemplary therapy device are similar to the techniques described in U.S. Pat. No. 6,178,562, the disclosure of which is herein incorporated for all purposes by reference.

Various aspects of the invention are similar to the subject matter described in: U.S. patent application Ser. No. 09/127,256 (filed Jul. 31, 1998) entitled, "Compliant Heat Exchange Panel" issued on Apr. 3, 2007 as U.S. Pat. No. 7,198,093; U.S. patent application Ser. No. 09/798,261 (filed Mar. 1, 2001) entitled, "Shoulder Conformal Therapy Component of an Animate Body Heat Exchanger" published on Aug. 30, 2001 as U.S. Publication No. 2001-0018604A1; U.S. patent application Ser. No. 09/901,963 (filed Jul. 10, 2001) entitled, "Compliant Heat Exchange Splint and Control Unit" published on Nov. 8, 2001 as U.S. Publication No. 2001-0039439A1; U.S. patent application Ser. No. 09/771,123 (filed Jan. 26, 2001) entitled, "Wrist/Hand Conformal Therapy Component of an Animate Body Heat Exchanger" published on Oct. 25, 2001 as U.S. Publication No. 2001-0034546A1; U.S. patent application Ser. No. 09/771,124 (filed Jan. 26, 2001) entitled, "Foot/Ankle Conformal Therapy Component of an Animate Body Heat Exchanger" published on Feb. 14, 2002 as U.S. Publication No. 2002-0019657A1; U.S. patent application Ser. No. 09/771,125 (filed Jan. 26, 2001) entitled, "Conformal Therapy Component of an Animate Body Heat Exchanger having Adjustable Length Tongue" published on Oct. 25, 2001 as U.S. Publication No. 2001-0034545A1; U.S. patent application Ser. No. 10/784,489 (filed Feb. 23, 2004) entitled, "Therapy Component of an Animate Body Heat Exchanger" published on Aug. 26, 2004 as U.S. Publication No. 2004-0167594A1 which is a continuation of U.S. patent application Ser. No. 09/765,082 (filed Jan. 16, 2001) entitled, "Therapy Component of an Animate Body Heat Exchanger and Method of Manufacturing such a Component" issued on Feb. 24, 2004 as U.S. Pat. No. 6,695,872 which is a continuation-in-part of U.S. patent application Ser. No. 09/493,746 (filed Jan. 28, 2000) entitled, "Cap And Vest Garment Components Of An Animate Body Heat Exchanger" issued on Jan. 30, 2001 as U.S. Pat. No. 6,178,562; U.S. patent application Ser. No. 10/122,469 (filed Apr. 12, 2002) entitled, "Make-Break Connector For Heat Exchanger" issued on Mar. 29, 2005 as U.S. Pat. No. 6,871,878; U.S. patent application Ser. No. 10/637,719 (filed Aug. 8, 2003) entitled, "Apparel Including a Heat Exchanger" issued on Sep. 19, 2006 as U.S. Pat. No. 7,107,629; U.S. patent application Ser. No. 12/208,240 (filed Sep. 10, 2008) entitled, "Modular Apparatus for Therapy of an Animate Body" published on Jan. 1, 2009 as U.S. Publication No. 2009-0005841A1 which is a divisional of U.S. patent application Ser. No. 10/848,097 (filed May 17, 2004) entitled, "Modular Apparatus for Therapy of an Animate Body" issued on Mar. 1, 2011 as U.S. Pat. No. 7,896,910; U.S. patent application Ser. No. 11/707,419 (filed Feb. 13, 2007) entitled, "Flexible Joint Wrap" issued on Nov. 23, 2010 as U.S. Pat. No. 7,837,638; U.S. patent application Ser. No. 11/854,352 (filed Sep. 12, 2007) entitled, "Make-Break Connector Assembly with Opposing Latches" issued on Jun. 8, 2010 as U.S. Pat. No. 7,731,244, which is incorporated herein for all purposes by reference.

The above systems generally provide active heating, cooling, and/or compression for humans and other animal bodies. They are used, for example, in physical therapy, pre-game conditioning, minor injury care, post-operative care, pain management, and emergency medical care, among other applications.

Thermal therapy systems exist in a number of different forms. In general, there is a control unit, a connector hose, a therapy wrap comprising a heat transfer device and a sleeve cover, and a power source (i.e., battery or externally-powered electric source). One will appreciate, however, that the system components and configuration may be modified depending on the application. The system may include a control unit for controlling administration of therapy using the therapy device. The system may also include other components such as fluidics, a power source, a cooling and/or heating source, a communications system, input/output devices, and a pump. The system may use gravity to fill the wrap instead of a fluid pump, or simply utilize a bladder that can be filled with ice and water which may be pressurized.

In order to provide two zone compression, the therapy wrap 200 has a hand wrap portion 210 and a forearm wrap portion 212, which can be integrated together into a single wrap, or in alternative embodiments, can be separate wraps that are applied independently. The forearm wrap portion 212 can have a first wing 214 and a second wing 216 that can be wrapped circumferentially around the patient's forearm. The proximal ends of the first wing 214 and the second wing 216 can have a greater width than the distal ends of the first wing 214 and the second wing 216 such that the forearm wrap portion 212 tapers in the distal direction. The tapered configuration facilitates improved conformance to the tapered nature of the patients forearm. The external surface of the sleeve can be covered with loop connectors 218 while the lateral edge of the interior surface of one of the first wing 214 or second wing 216 can have hook connectors 220. The hook and loop connectors can be used to fasten the forearm wrap portion 212 securely around the patient's forearm so that the pressure is directed towards the patient's skin rather than ballooning outwards. One may also appreciate that this invention may also be applied to other regions of the body, such as the foot and/or ankle.

The hand wrap portion 210 can have a palm facing portion 222 and a hand covering portion 224 that can be folded over the top of the hand. The lateral portions of the interior surface of the palm facing portion 222 can have hook fasteners that can secure the hand covering portion 224, which can have an exterior surface having loop connectors, over the patient's hand. In order to limit or resist circumferential compression in the hand wrap portion 210, a base plate 228 that functions to resist compression from the medial and lateral directions can be placed within the sleeve 202, thereby translating the applied pressure into a flat pressure. By placing the base plate 228 within the sleeve 202 in the hand wrap portion 210, the tendency of the hand wrap portion 210 to become cylindrical is reduced or prevented. However, because the flat pressure applies pressure to the top and bottom of the hand, the flat pressure tends to flatten out the hand.

In order to prevent the hand from adopting a flat configuration when flat pressure is applied to the hand, the therapy wrap 200 can have a hand support 226 that is sized and shaped to fit within the patient's hand when the hand is in the relaxed, unstressed configuration shown in FIG. 1. For example, the hand support 226 can have a convex, curved palm facing surface that conforms to the patient's palm and fingers in the natural, relaxed, unstressed configuration of the hand. The hand support 226 can have a flat base that can provide stability while sliding against the base plate 228. The hand support 226 can be made of a structurally resilient or compliant material such as a foam or gel that can support the natural unstressed structure of the hand while providing an ergonomic surface. In other embodiments, the hand support 226 can be made of a more solid material such as a plastic or metal. In some embodiments, the hand support 226 can be made of a thermally conductive material such as a metal. The hand support 226 can be slidably fastened to the base plate 228 to allow the position of the hand support 226 to be adjusted until the hand support 226 is resting under the patient's hand. In some embodiments, the hand support 226 is adjacent and/or in contact with the base plate 228. In some embodiments, the hand support 226 can be affixed to the base plate such that the position of the hand support 226 relative to the base plate 228 is fixed. In other embodiments, the hand support 226 can be integrated with the base plate. In some embodiments, the hand support may come in a variety of shapes and sizes, or may be malleable and adjustable by the user. Additional support may also include the wrist and/or forearm. For example, the base plate 228 can be extended proximally to include a support for the wrist and/or forearm. Such additional support may be integrated into the base plate, or be separate components. The additional supports may also be adjustable to provide a multiplicity of support positions.

Figure 3A:
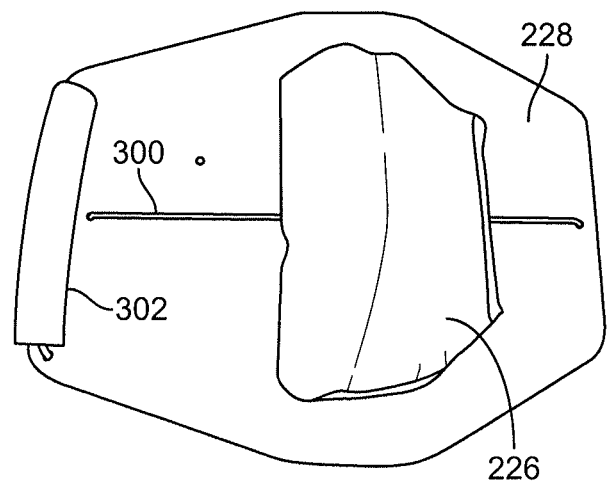
FIGS. 3A-3F illustrate the assembly of an embodiment of a hand wrap.
Figure 3B:
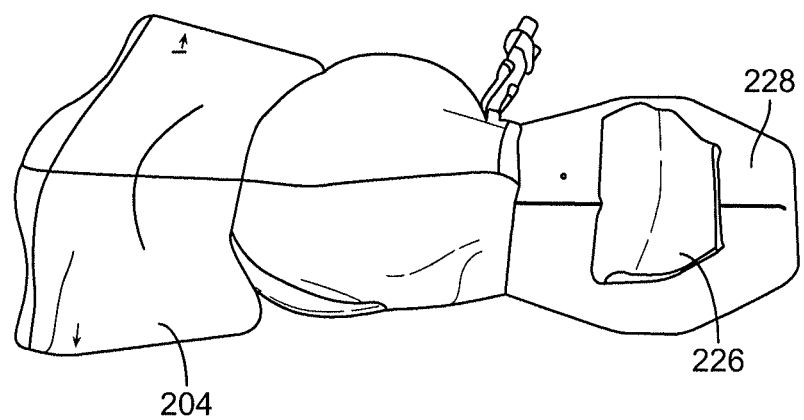

FIGS. 3A and 3B illustrate an embodiment of a hand support 226 that is slidably attached to a base plate 228 using a tether 300. The tether 300 can be attached to the base plate 228 along a central longitudinal line that bisects the base plate 228 and is transverse to a cylindrical retaining member 302. The hand support 226 can be slidably attached to the tether such that the position of the hand support 226 can be adjusted to fit the patient, while maintaining the alignment of the hand support 226. In addition, the tether 300 functions to prevent loss or misplacement of the hand support 226. In some embodiments, the tether 300 is removably attached to the base plate 228 to allow disassembly and cleaning and/or replacement of various components of the device, or to allow substitution of a different sized component or removal of a component from the device.

The base plate 228 can have a shape and size that can function to both support the hand and securely reside within a pocket in the hand wrap portion 210 of the sleeve 202. The base plate 228 can be stiff and strong enough to resist the applied wrap pressures without significant deflection or breaking. In some embodiments, a $1/16"$ to $1/8"$ thick plastic base plate is adequate. In other embodiments, the base plate 228 can be made of a different material, such as a metal, which can also conduct heat from the heat exchanger.

In some embodiments, the hand support 226 and/or base plate 228 can be placed within the sleeve such that the heat exchanger 206 is positioned between the hand support 226/base plate 228 and the patient's hand. In this configuration, the heat exchanger 206 is positioned closer to the patient's hand and therefore may be able to provide more efficient heating or cooling. In other embodiments, the hand support 226/base plate 228 can be placed between the heat exchanger 206 and the patient's hand, and in this embodiment, the hand support 226 and base plate 228 can be made of a thermally conductive material such as metal so that the cooling and heating function of the heat exchanger 206 can be transmitted through the hand support 226 and base plate 228. In this configuration, the patient's hand is closer to the hand support 226 and may be maintained in the relaxed, unstressed configuration more easily even when the compressive element is activated. In some embodiments, there is no compressive element 208, such as an air bladder, directly under the patient's hand in the palm facing portion of the therapy component 204 of the therapy wrap 200. There can still be a compressive element in the hand covering portion that goes on top of the patient's hand. Such a configuration enhances the conformation of the patient's hand to the hand support 226.

Figure 3C:
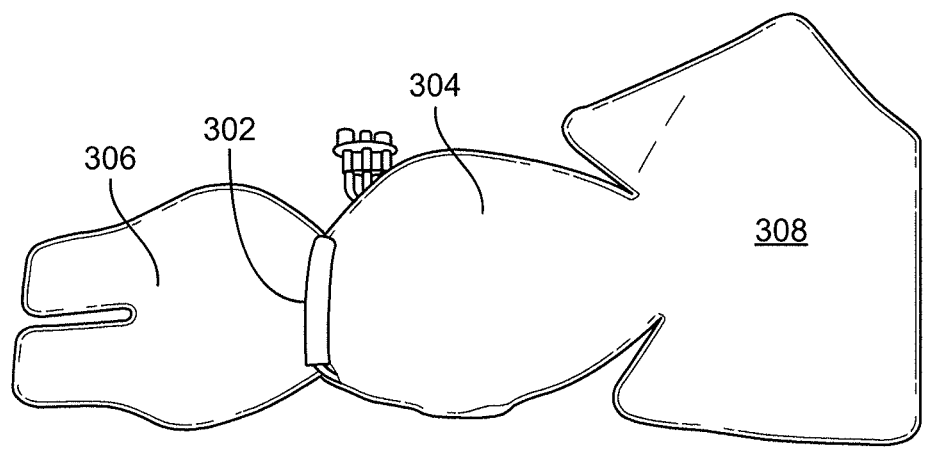
Figure 3D:
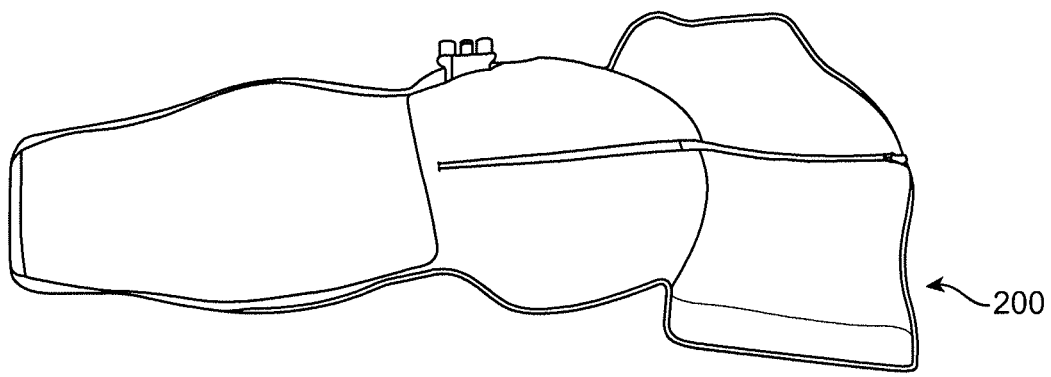

As illustrated in FIG. 3C, the base plate 228 can have a cylindrical retaining member 302 that forms a slot with the base plate 228. The therapy component 204, which includes the heat exchanger 206 and the compressive element 208, can be inserted partially through the slot such that the base plate 228 is secured to the therapy component 204. The therapy component 204 can have a structure that corresponds to the sleeve 202 and therapy wrap 200. For example, the therapy component 204 can have a palm portion 304 and hand covering portion 306 and a forearm portion 308 that are sized and shaped to fit within corresponding pockets within the sleeve 202. After the therapy component 204 is inserted through the slot and secured to the base plate 228, the therapy component 204 and base plate 228 and hand support 226 can be inserted into the sleeve to form an assembled therapy wrap 200, as illustrated in FIG. 3D, with the hand support 226 facing the interior surface of the sleeve 202 in the palm facing portion 222 of the therapy wrap 200.

Figure 2A:
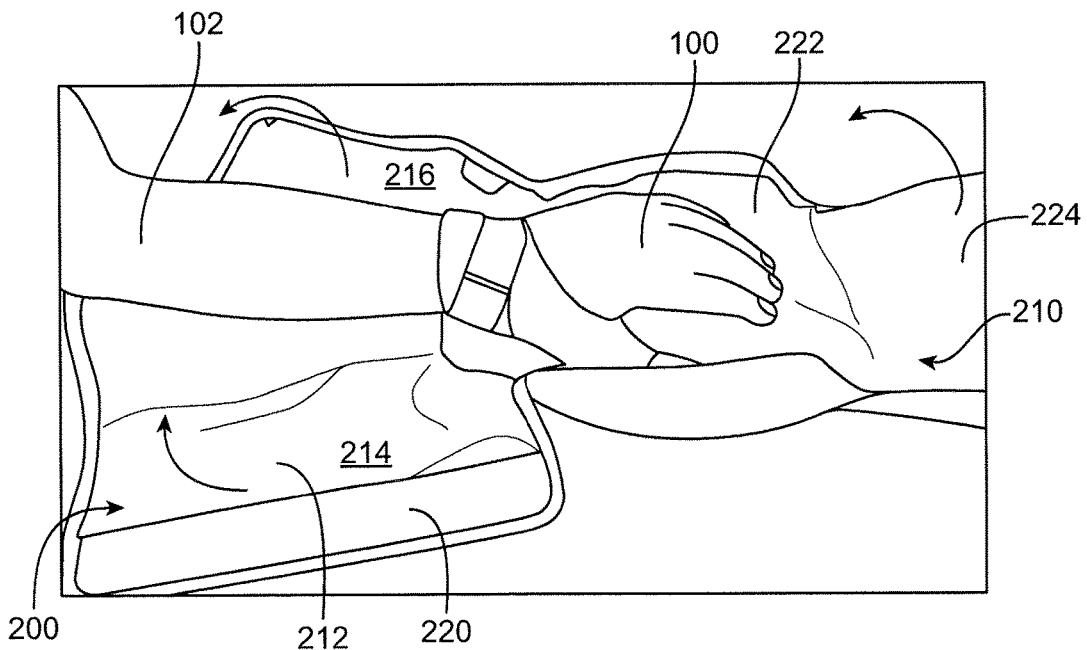
FIGS. 2A-2D illustrate an embodiment of a hand wrap that includes a sleeve, a therapy component, a base plate and a hand support.
Figure 2B:
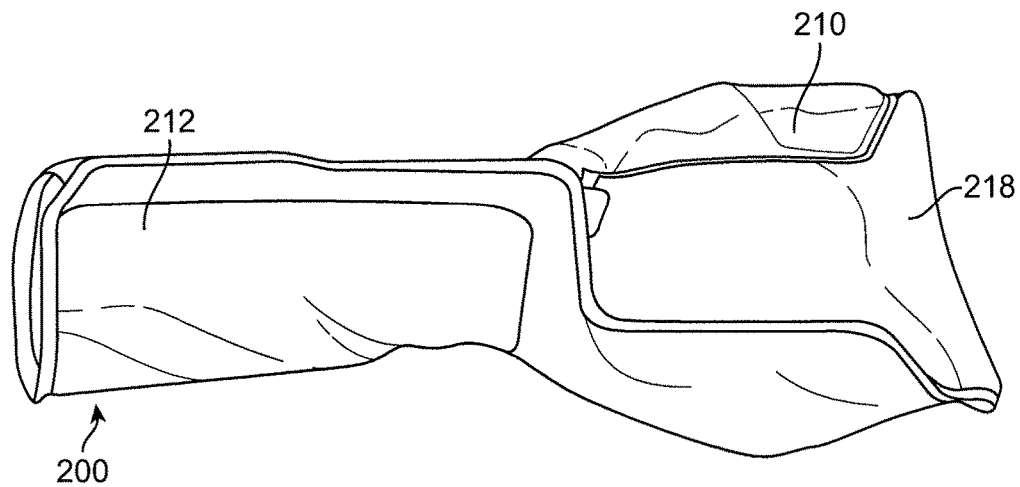
Figure 3E:
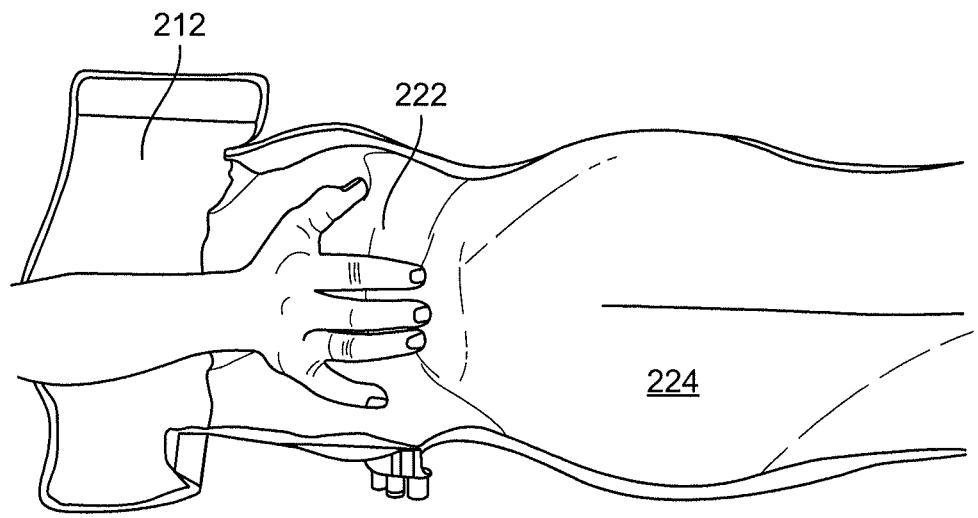
Figure 3F:
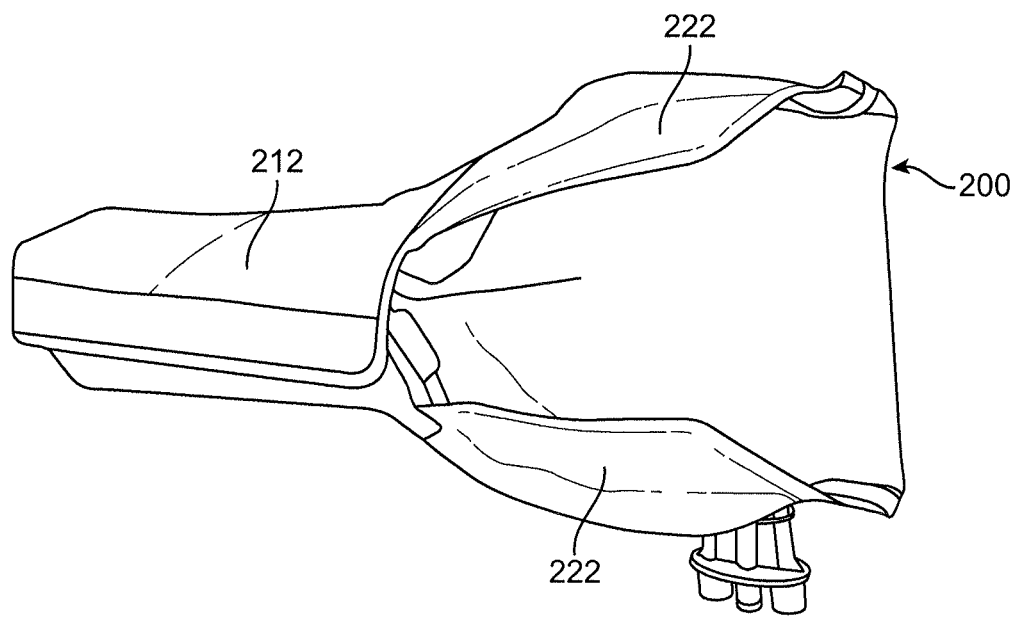

As illustrated in FIGS. 2A, 3E and 3F, to wrap the therapy wrap 200 over the patient's forearm 102 and hand 100, the patient can lay his forearm 102 over the forearm wrap portion 212 and can lay his hand 100 over the palm facing portion 222 of the therapy wrap 200. The patient's hand can grasp and manipulate the hand support 226 within the sleeve 202 until the hand support 226 is located in a comfortable position. The hand cover portion 224 can then be folded over the patient's hand 100 and a distal portion of the forearm 102, and lateral wings on the forearm wrap portion 212 and palm facing portion 222 can be wrapped around the patient's forearm and hand to secure the wrap to the patient, using for example, hook and loop connectors as described above. Other fastening mechanisms, such as straps and buckles, can be also used.

In some embodiments, as illustrated and described herein, the sleeve 202 is removable from the therapy component 204 in order to facilitate cleaning and/or replacement of various components. The sleeve 202 can also provide the structural support that directs compression towards the skin. The palm facing portion 222 of the sleeve 202 has a close fitting pocket for receiving the palm facing portion of the therapy component 204 and the hand support 226 and the base plate 228. If the pocket is too spacious, the air bladder of the compressive element 208 may tend to push the hand support away from the palm and flatten the hand. Therefore, the pocket of the sleeve can have a close fit with at least two edges of the base plate 228, such as the medial and lateral edges, while having enough room to also fit the hand support and the therapy component.

In some embodiments, the base plate 228 can be attached to the sleeve 202 in order to prevent or reduce misalignment or misplacement. For example, the base plate can be attached to the sleeve using a variety of attachment techniques, such as a hook and loop fastener, buttons, adhesives, sutures, and the like. In addition, the base plate can be shaped to facilitate proper placement in the sleeve, such as having a distinct or unique shape that corresponds to a pouch in the sleeve having a matching shape.

Figure 2C:
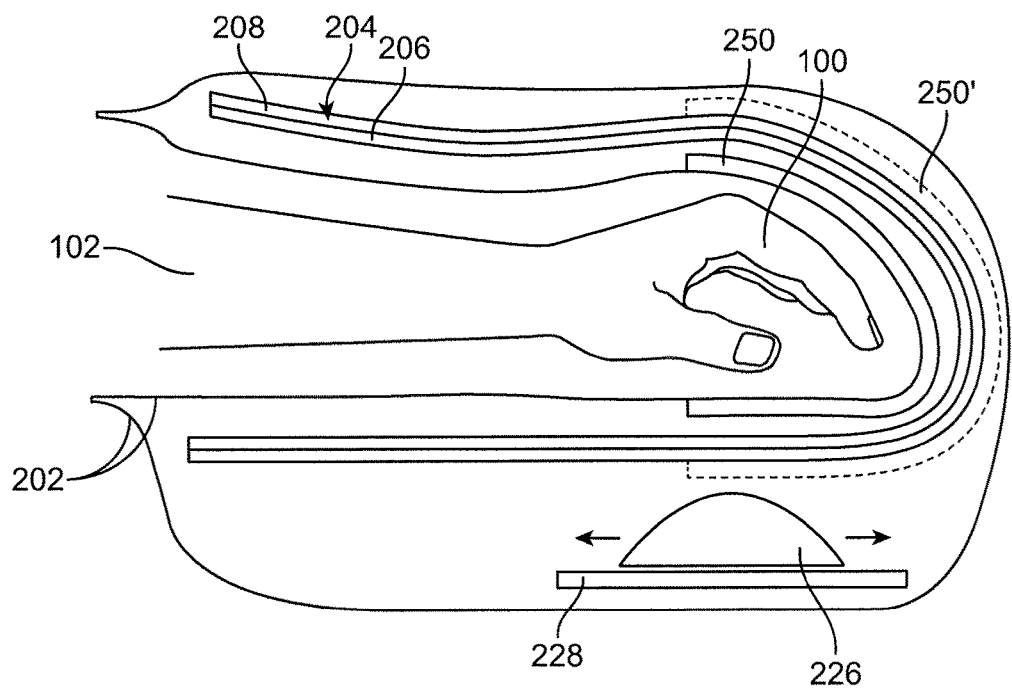
Figure 2D:
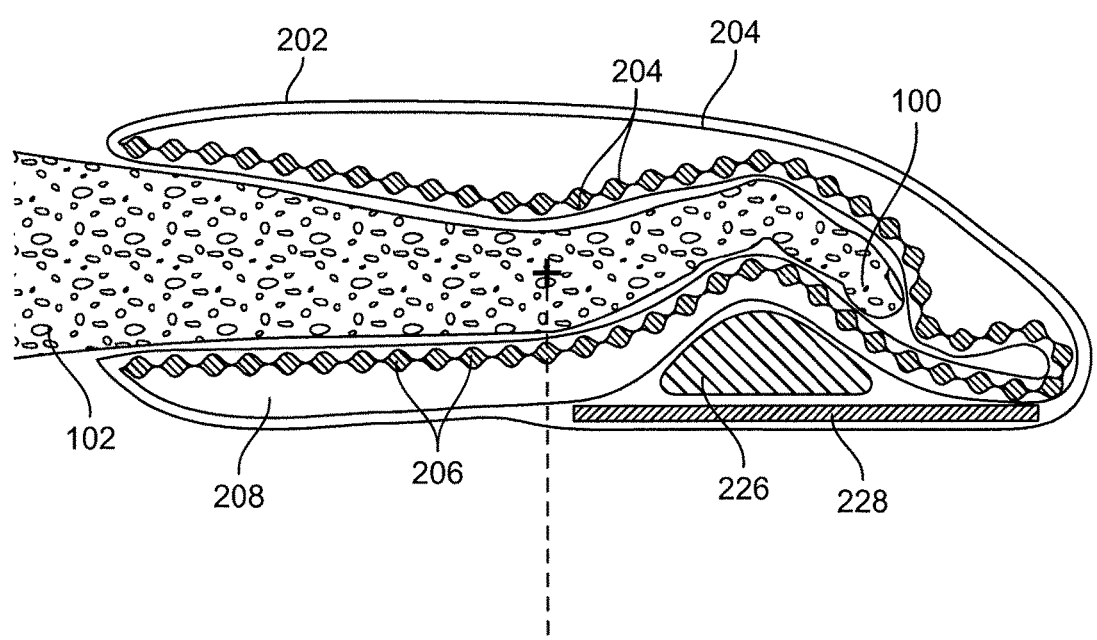
Figure 4A:
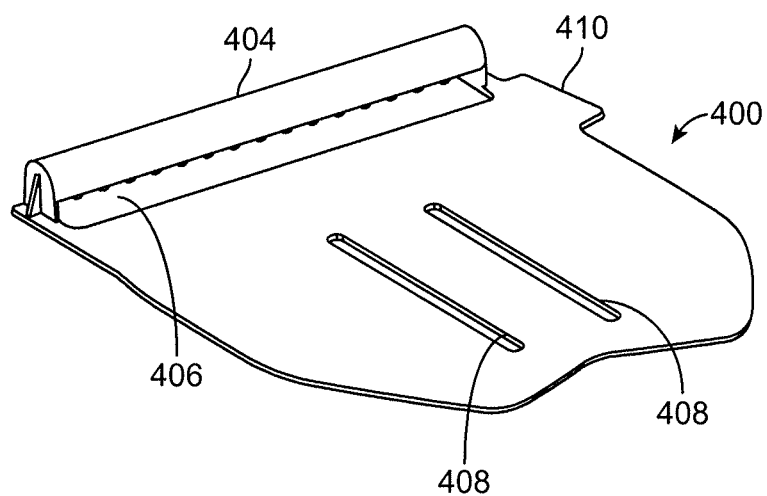
FIGS. 4A-4U illustrate alternative embodiments of base plates and hand supports that can be used in a hand wrap.
Figure 4B:
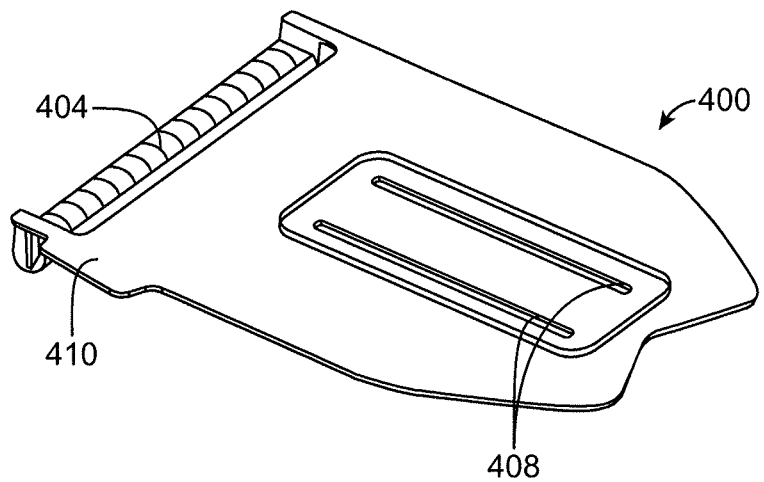
Figure 4C:
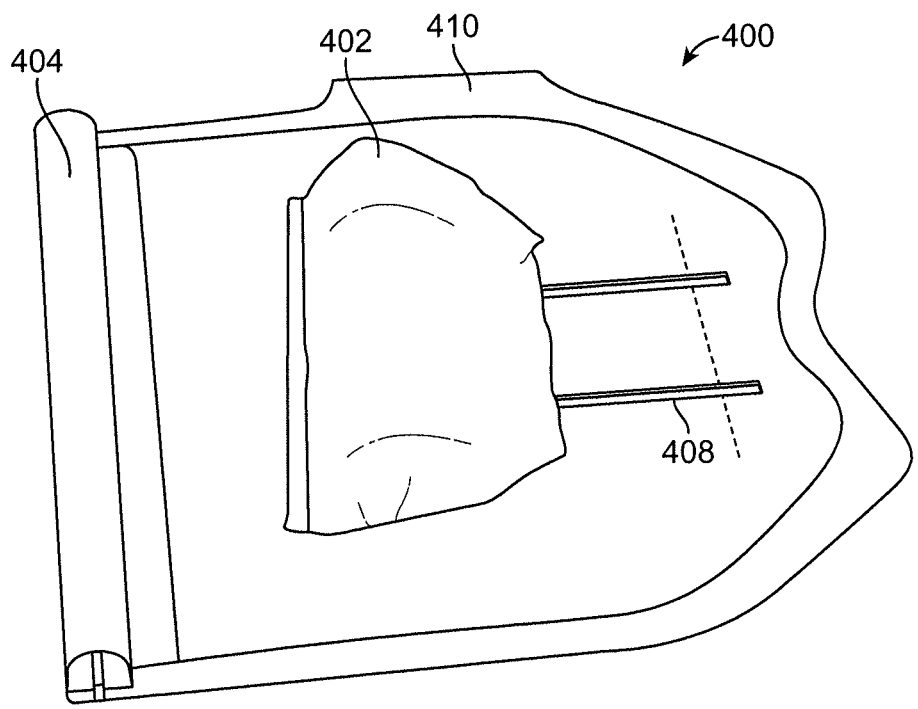
Figure 4D:
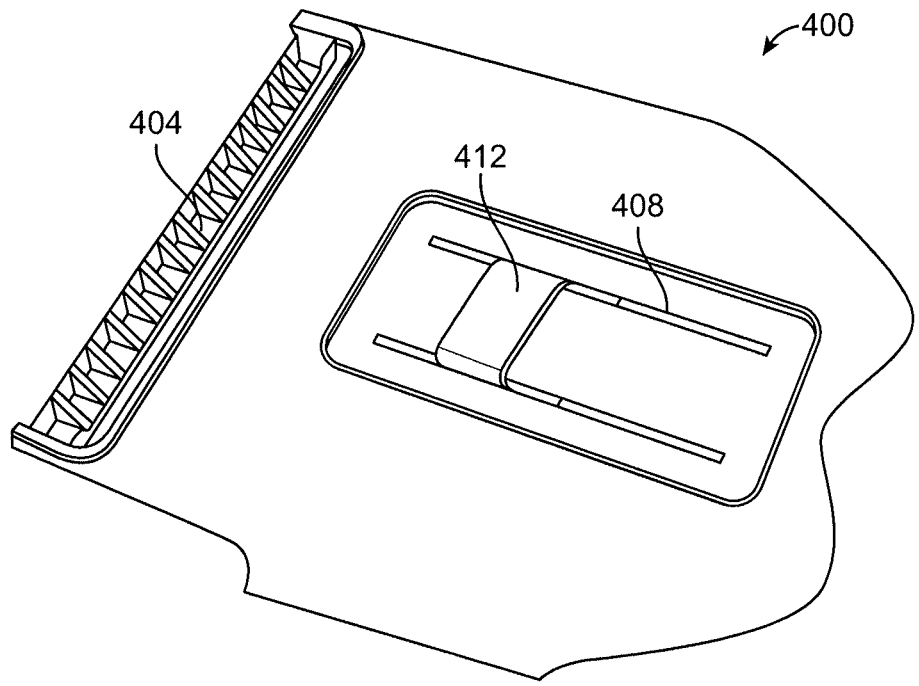
Figure 4E:
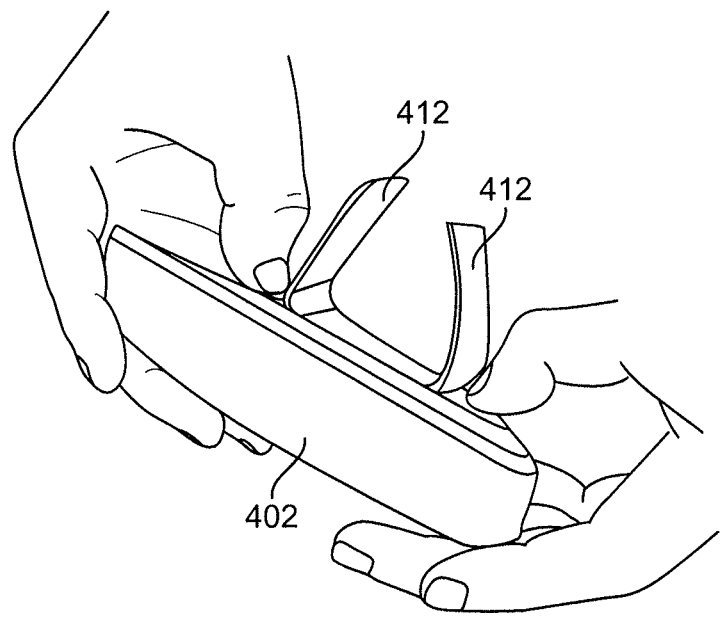
Figure 4F:
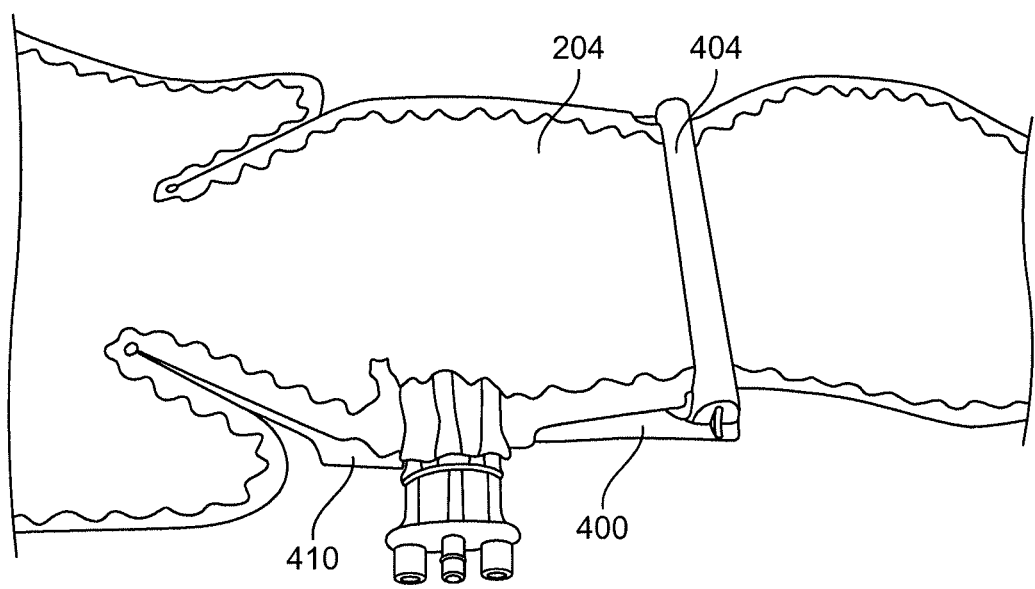
Figure 4G:
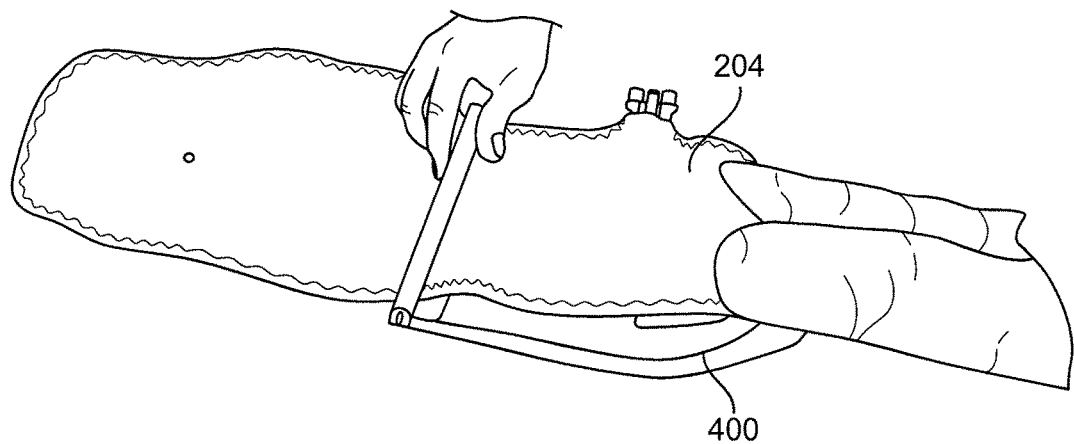
Figure 4H:
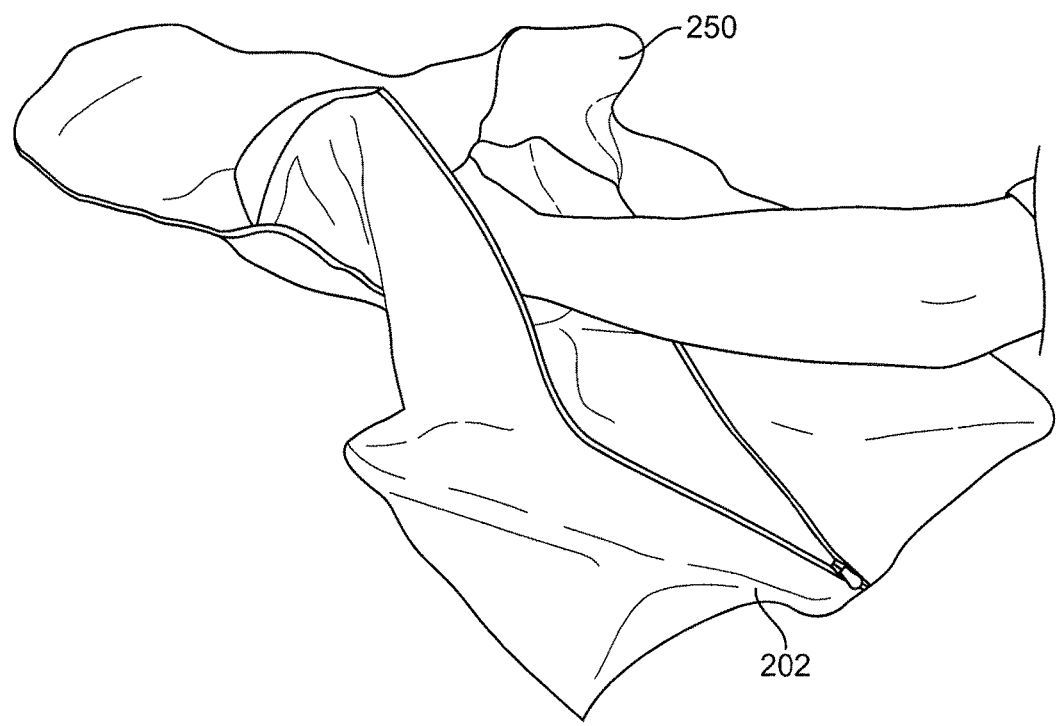
Figure 4I:
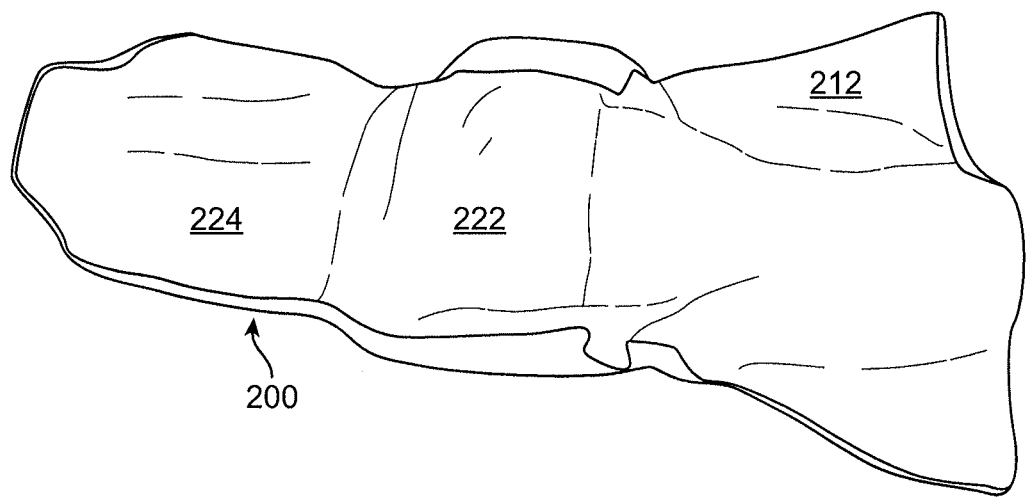
Figure 4J:
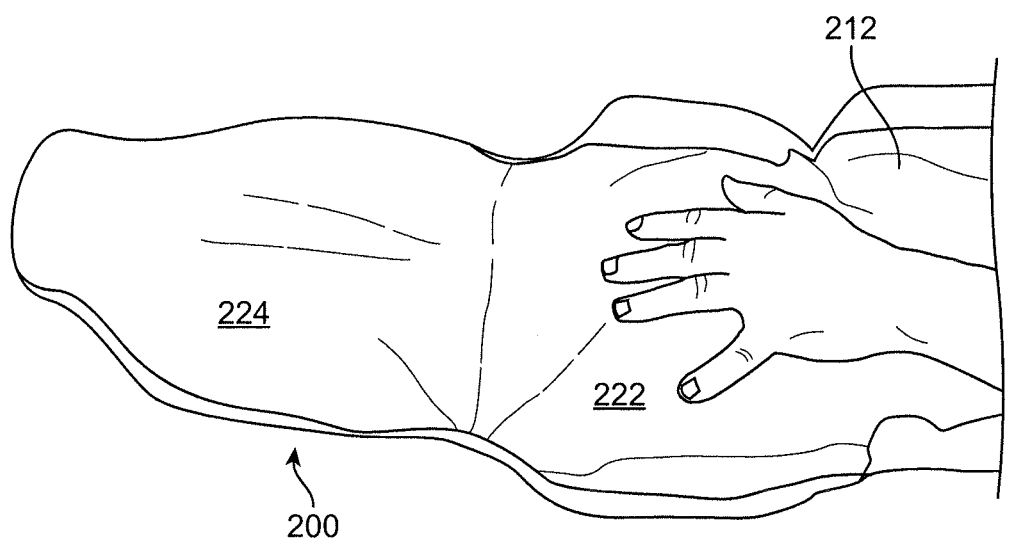
Figure 4K:
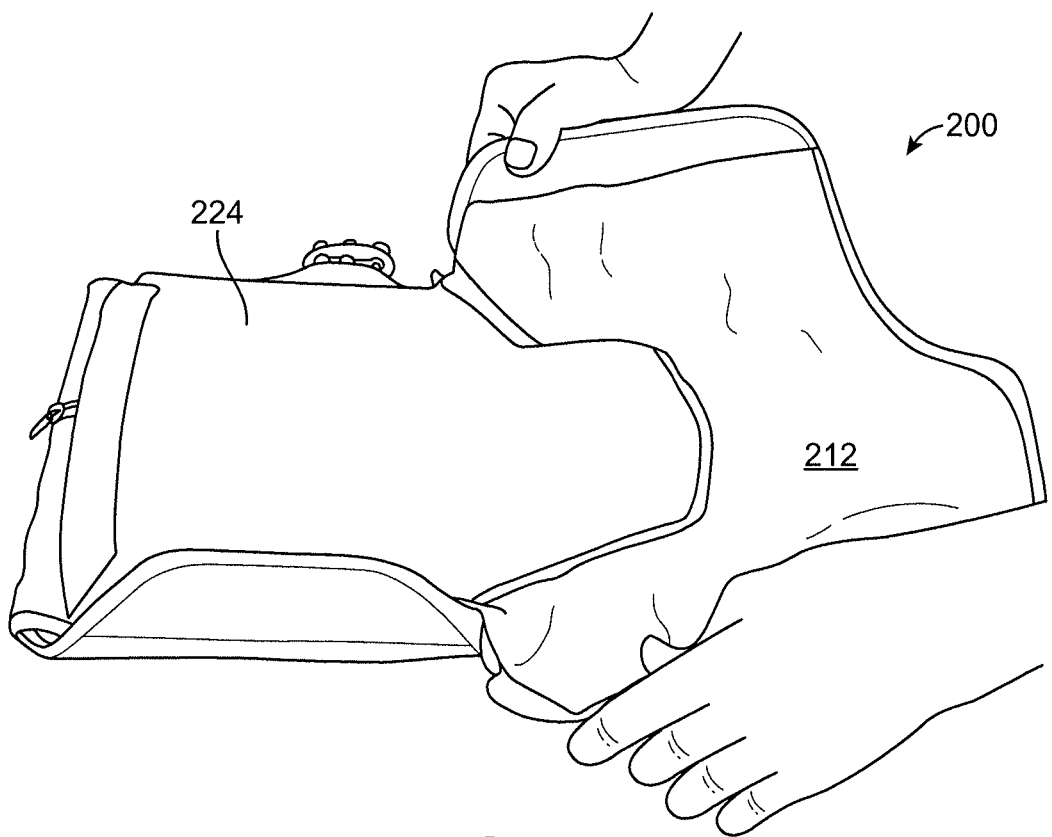
Figure 4L:
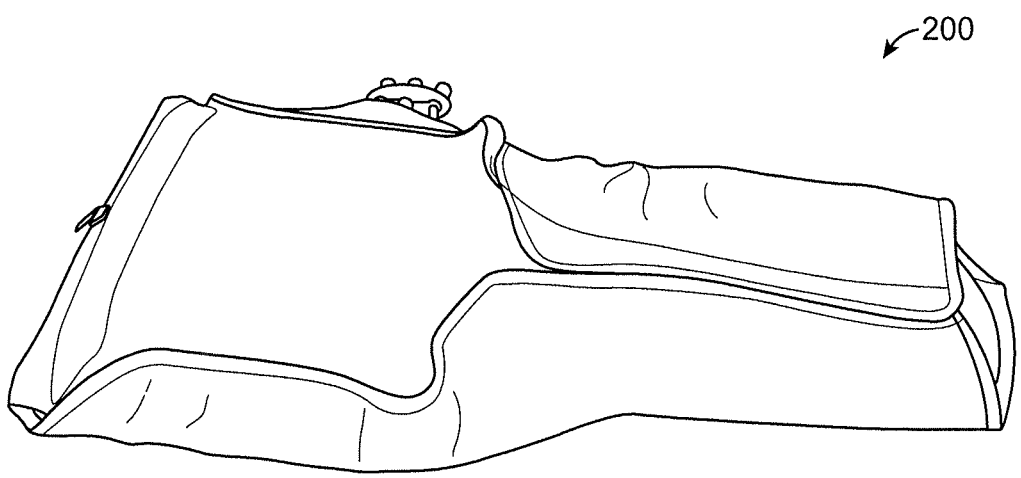
Figure 4N:
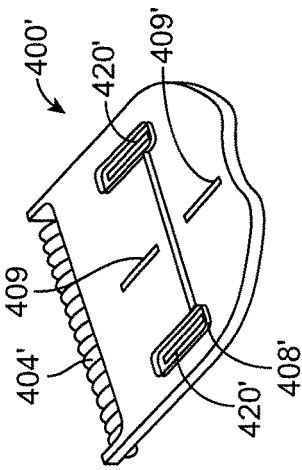
Figure 4P:
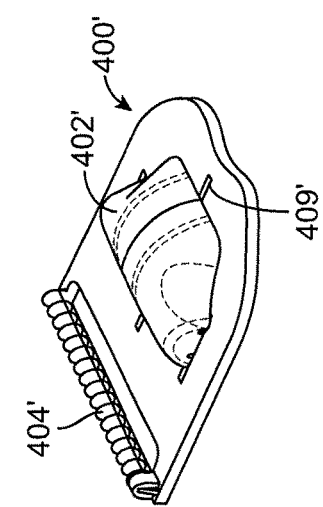
Figure 4M:
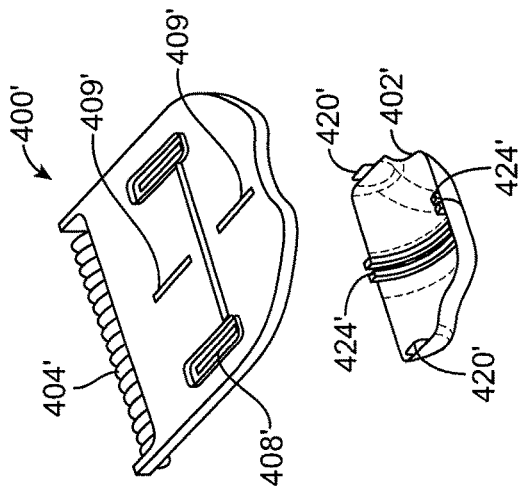
Figure 4O:
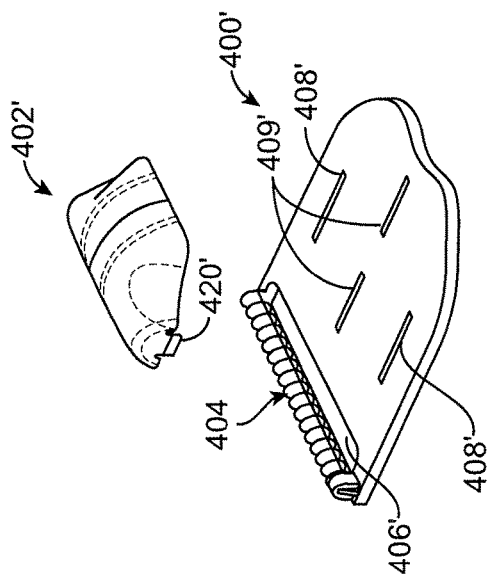
Figure 4Q:
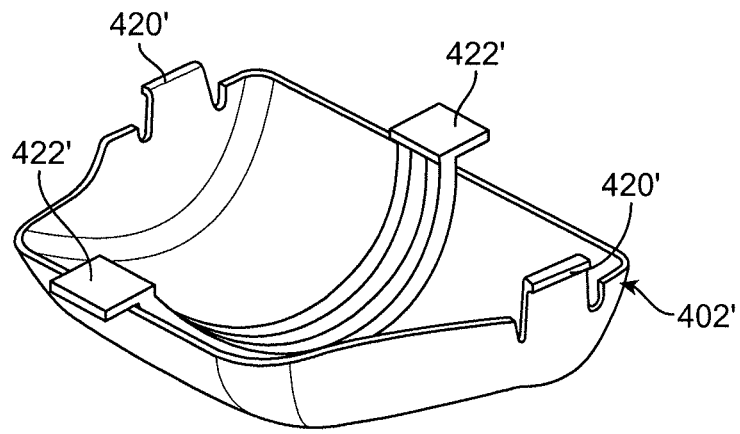
Figure 4R:
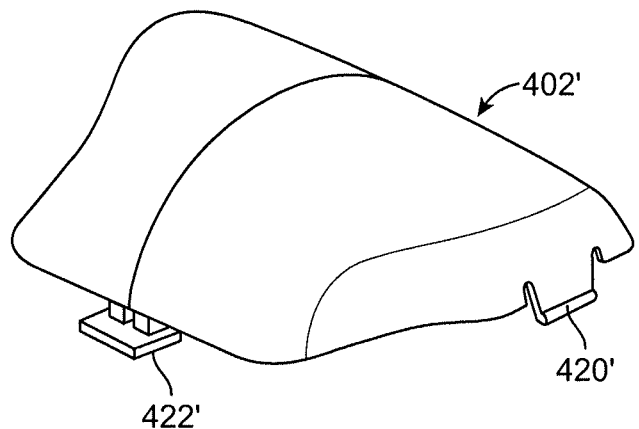
Figure 4S:
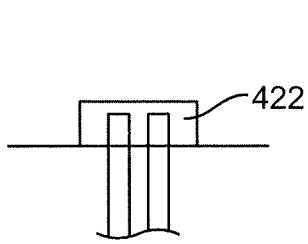
Figure 4T:
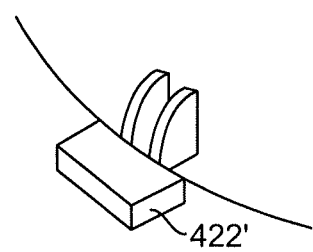
Figure 4U:
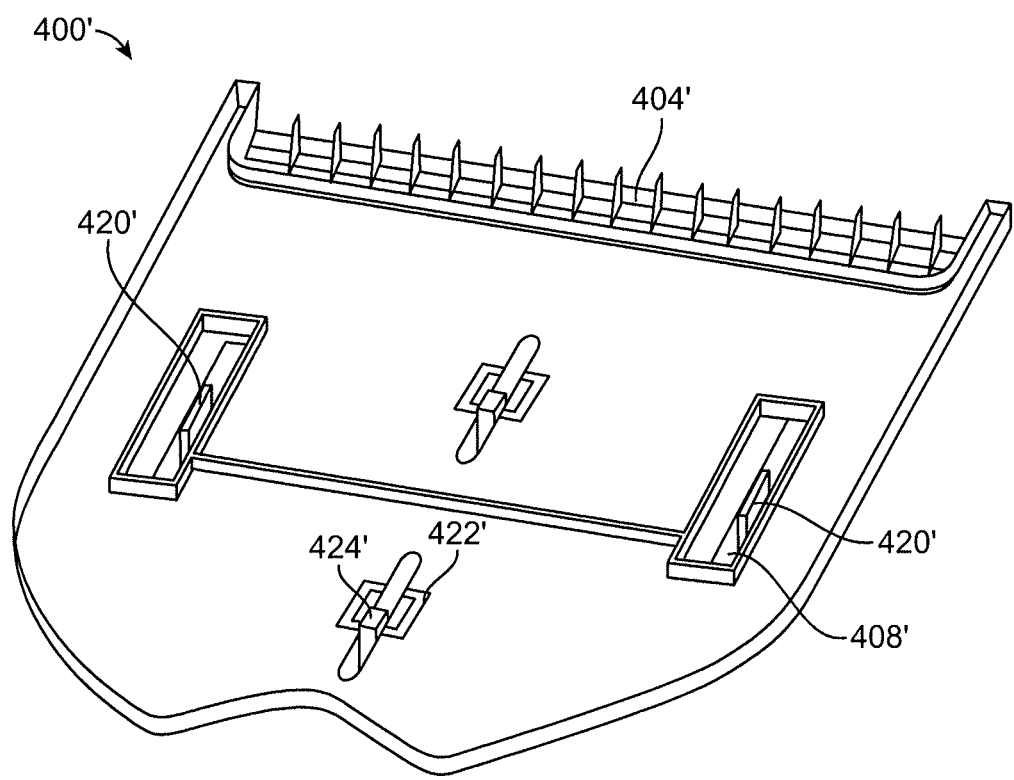
Figure 5A:
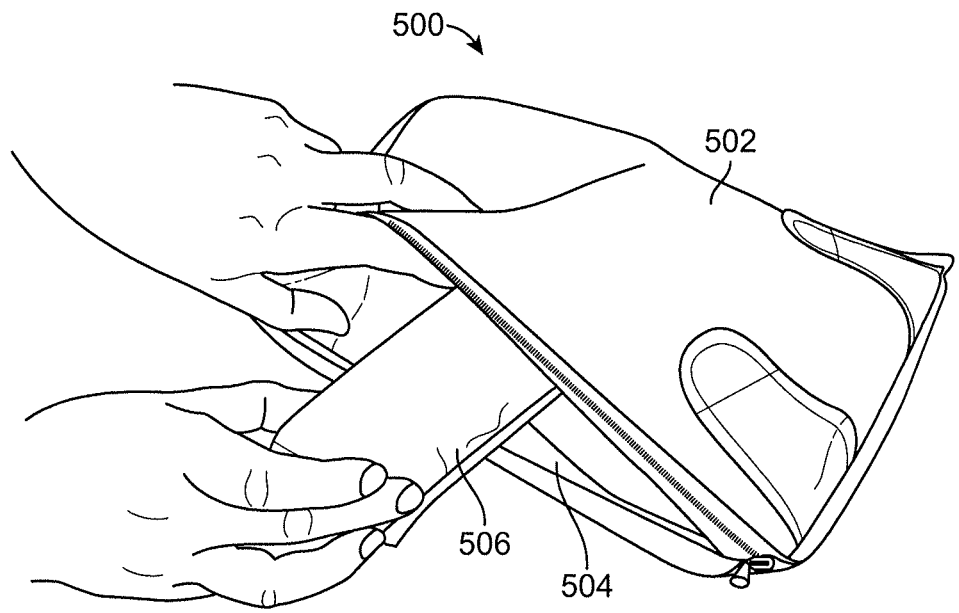
FIGS. 5A-5E illustrate another embodiment of a hand wrap.
Figure 5B:
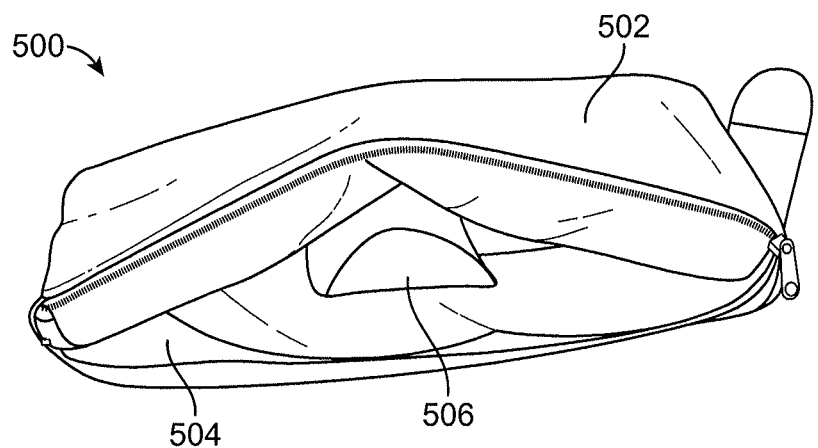
Figure 5C:
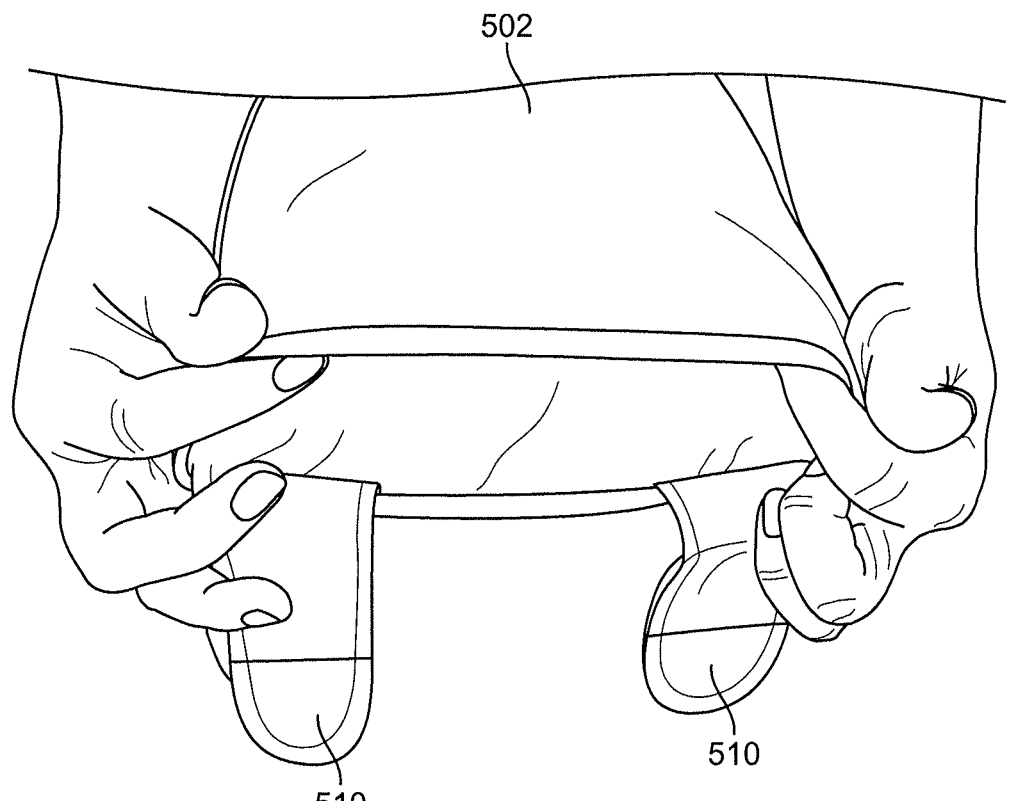
Figure 5D:
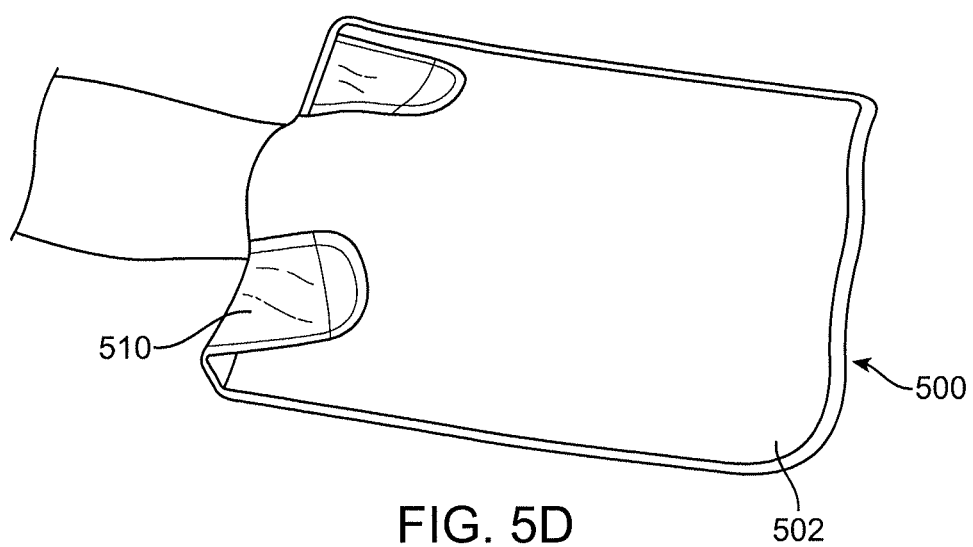
Figure 5E:
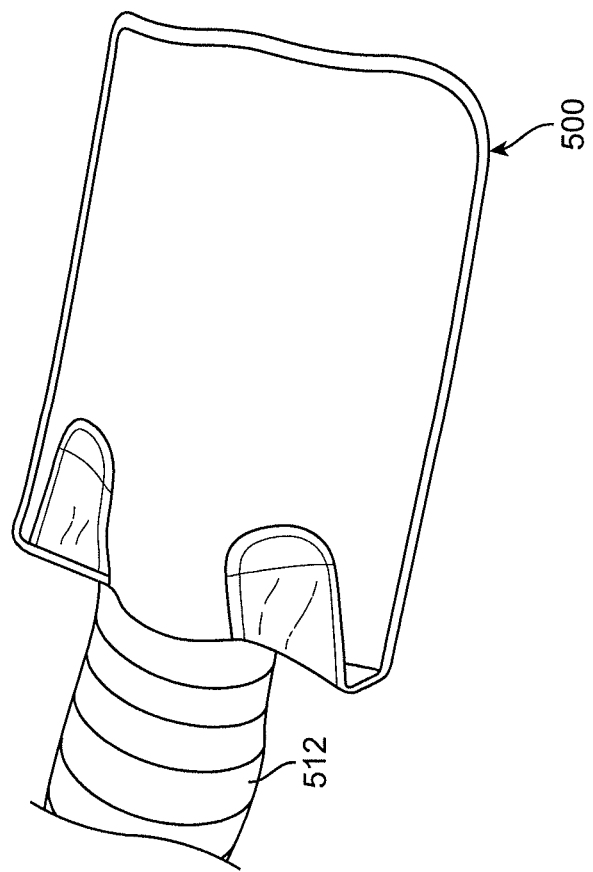

In some embodiments, as shown in FIG. 2C and FIG. 4H, the sleeve 202 may include one or more thermal insulating members 250 that can be placed in the palm facing portion 222 and/or the hand covering portion 224 of the sleeve 202. In some embodiments, the insulating member 250 can be placed within the sleeve 202 and adjacent to the interior surface side of the sleeve such that the insulating members cover one or both sides the patient's fingers when the therapy wrap 200 is wrapped around the patient's hand. In some embodiments, the insulating members can be removably placed within the pockets of the sleeve, while in other embodiments, the insulating member 250 can be permanently attached to the sleeve, by for example stitching the lateral edges of the insulating member 250 to the sleeve 202. The insulating members function to limit cooling to the patient's fingers, which may be more sensitive to cold temperatures. The insulating member may have a curved perimeter to approximate that of the finger/palm joints. In some embodiments, as shown in FIG. 4H, the insulating member 250 is attached to the interior of the sleeve 202 in a manner that divides the palm facing portion 222 and the hand covering portion 224 into two compartments that are both capable of receiving the therapy component. This can be accomplished by stitching the lateral edges of the insulating member 250 to the interior of the sleeve 202, as described above. Such a configuration allows the insulating member 250 to be put in use or not put in use by simply inserting the therapy component 204 into one of the two compartments. As shown in FIG. 2C, if the insulating member 250 is between the therapy component 204 and the patient's fingers, the insulating member 250 is being used. If the insulating member 250 is not between the therapy component 204 and the patient's fingers, i.e. the therapy component 204 is between the insulating member 250 and the patient's fingers, then insulating member 250 is not being used to insulate the patient's fingers. In FIG. 2C, the non-used insulating member 250' is shown in dotted lines which depict the alternative placement described above. In other embodiments, the patient may be provided with an insulating glove, towel, or mitt that can be worn over the fingers and that can be optionally installed within the hand wrap.

In some embodiments, the therapy device 200 can be sleeveless, and can instead include the therapy component 204, the base plate 228 and the hand support 226. The base plate 228 can be attached directly to the air bladder of the compressive element 208 and/or to the perimeter of the heat exchanger 206. Straps and/or hook and loop fasteners or other securing mechanisms can be added to the therapy component 204 to allow the therapy component to be directly secured to the patient's forearm and hand.

FIGS. 4A-4E illustrate another embodiment of a base plate 400 and hand support 402. The base plate 400 also has a cylindrical or partially cylindrical retaining member 404 that forms a slot 406 with the base plate 400. The cylindrical retaining member 404 functions to prevent or reduce kinks in the therapy component 204 that may form when the therapy component is folded over the hand by providing a smooth rounded surface over which the therapy component can be folded, thereby reducing or preventing sharp folds or creases from forming. The base plate 400 may also have hose connector support structure 410 which can extend laterally out of side of the base plate 400. The hose connector support structure 410 is aligned with and functions to support the tubing or hose connect of the therapy component 204 when the therapy component is inserted through the slot 406 in the base plate 400. By supporting the hose connector, the hose connector support structure 410 can reduce or prevent kinking of the hose connector and/or hoses extending from the therapy component. The base plate 400 can also have two parallel slots 408 that extend across the base plate 400 transversely to the retaining member 404. The slots 408 can be used to slidably secure the hand support 402 to the base plate 400 while maintaining the proper orientation of the hand support 402. The spacing of the slots 408 provides additional stability to the slidably attached hand support 402 and enhances its ability to resist torsion and misalignment. The hand support 402 can have a pair of straps 412 that extend from the base of the hand support 402 and that are spaced apart the same distance as the slots 408. In some embodiments, the pair of straps 412 can be formed by securing the middle portion of a single strap to the base of the hand support such that the two ends of the single strap become the pair of straps. To secure the hand support 402 to the base plate 400, the straps 412 can be inserted through the slots 408 and reversibly secured together, using a hook and loop connector, for example.

FIGS. 4F-4L illustrate a method of assembling the therapy wrap 200, which is similar to the method described above. As shown in FIGS. 4F and 4G, the therapy component 204 is inserted through the slot 406 of the base plate 400 such that the hand facing portion of the therapy component 204 lies over the base plate and the hose connector lies over the hose connect support structure 410. The therapy component 204, base plate 400 and hand support 402 can then be reversibly inserted into the sleeve 202 through, for example, a zippered opening running along the length of the exterior surface of the sleeve. FIGS. 4I-4L illustrate a method of wrapping and securing the therapy wrap 200 to a patient's forearm and hand, which is the same as described above.

FIGS. 4M-4U illustrate another embodiment of a base plate 400' and hand support 402'. The base plate 400' and hand support 402' are similar to the base plate 400 and hand support 402 describe above with reference to FIGS. 4A-4E, and can be used with the sleeve 202 and therapy wrap 204 to assemble a therapy wrap 200 as described herein. The base plate 400' can have two parallel slots 408' that are spaced out towards the lateral sides of the base plate 400'. In addition, the base plate 400' can have two additional keyhole slots 409' that lie on a longitudinal line that bisects the base plate 400'. The hand support 402' can have a curved, ergonomic top portion that conforms to the natural, unstressed configuration of the hand, with the distal end of the top portion being wider than the proximal end of the top portion. The narrower proximal end supports the patient's palm while the wider distal end supports the patient's fingers. Extending from the lateral sides of the base of the hand support 402' are a pair of clips 420' that can be reversibly inserted into the slots 408' to slidably secure the hand support 402' to the base plate 400'. Additional securement can be provided by tabs 422' located at the center of the proximal and distal ends of the base plate 400'. These tabs 422' can be reversibly attached to the base plate 400' on slot guides 424' that fit through the additional slots 409' located on the center of the base plate 400'. The tabs 422' can be wider than the slots 409' and therefore can be used to secure the hand support 402' to the base plate 400'. The slot guides 424' can be formed from a single rib or a double rib for increased strength. Use of a double rib may require use of wider slots 409' to accommodate the double rib or use of double slot design. In some embodiments, the hand support 402' may be fabricated as a thin shell in order to reduce material costs.

Another difference in this embodiment of the base plate 400' is the cross bar or retaining member 404' which can be cylindrical or partially cylindrical to present a curved surface to the therapy component 204 that is wrapped around the retaining member 404'. To provide additional room for the patient's fingers, material can be removed from the retaining member and/or a different shape can be used, such as a curved shell. The retaining member may also be spaced further from the hand support to provide additional room. In some embodiments, the retaining member 404' can additionally have a plurality of ribs 426' or projections that wrap circumferentially around discrete locations along the length of the retaining member 404, forming an uneven surface across the retaining member that includes peaks at the ribs 426' and depressions or grooves between the ribs 426'. The uneven surface across the retaining member 404' further reduces or prevents kinking of the therapy component 204 by providing spaces between the ribs that can allow fluid to flow even when the therapy component 204 is pressed tightly against the retaining member 404'.

The hand wraps described above can provide compression to the hand with reduced pressure or compression from the medial and lateral directions, while still providing supported compression to the posterior and anterior portions of the hand. This type of compression can reduce swelling while providing enhanced contact between the hand wrap and the skin, which improves thermal treatment efficiency from the heat exchanger. In addition, the natural, unstressed position of the hand is maintained during treatment, which reduces pain and/or damage to the patient's hand.

FIGS. 5A-5F illustrate an alternative embodiment of a hand wrap 500 that has an mitt 502, a therapy component disposed within the mitt 502, a base plate 504 removably disposed within the palm facing portion of the mitt 502 and a hand support 506 also removably disposed within the palm facing portion of the mitt 502 such that the hand support is between the patient's hand and the base plate 504. The palm facing portion of the mitt 502 can be accessed through a zippered opening along one side of the mitt 502. The mitt 502 can have an opening 508 to receive that patient's hand. Two straps 510 positioned at the sides of the opening 508 can be used to tighten and secure the hand wrap to the patient's hand. In some embodiments, a forearm wrap 512 can be additionally used to provide thermal and/or compressive therapy to the patient's forearm.

Figures 6A, 6B:
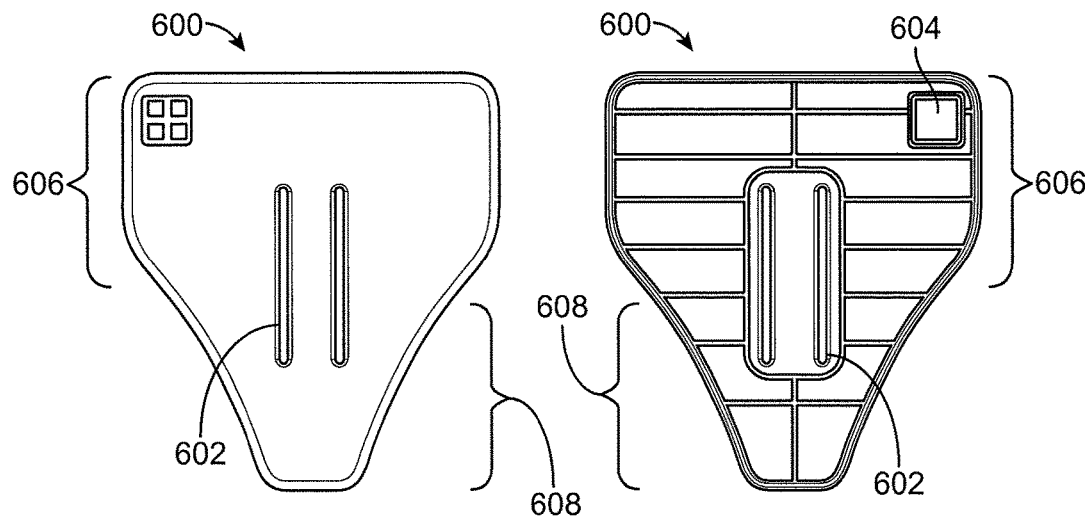
FIGS. 6A and 6B illustrate top and bottom views of an embodiment of a base plate.

FIGS. 6A and 6B illustrate an embodiment of the base plate 600 having a pair of parallel slots 602 centered along the longitudinal axis of the base plate 600 and an attachment feature 604 on the bottom side of the base plate 600. The base plate 600 can have a hand support portion 606 and a wrist support portion 608 that tapers from the wider hand support portion. The attachment feature 604 may allow the base plate to be removably attached to the inside lining of the sleeve. For example, the attachment feature 604 can be a plurality of hooks that can attach to complementary loops on a predetermined location on the inside lining of the sleeve. Other attachment features can also be used, such as a button, magnet, clasp, and the like. The attachment feature 604 can be offset from the center of the base plate, such as positioned at a corner, to facilitate proper orientation of the base plate within the sleeve.

Figures 7A, 7B, 7C:
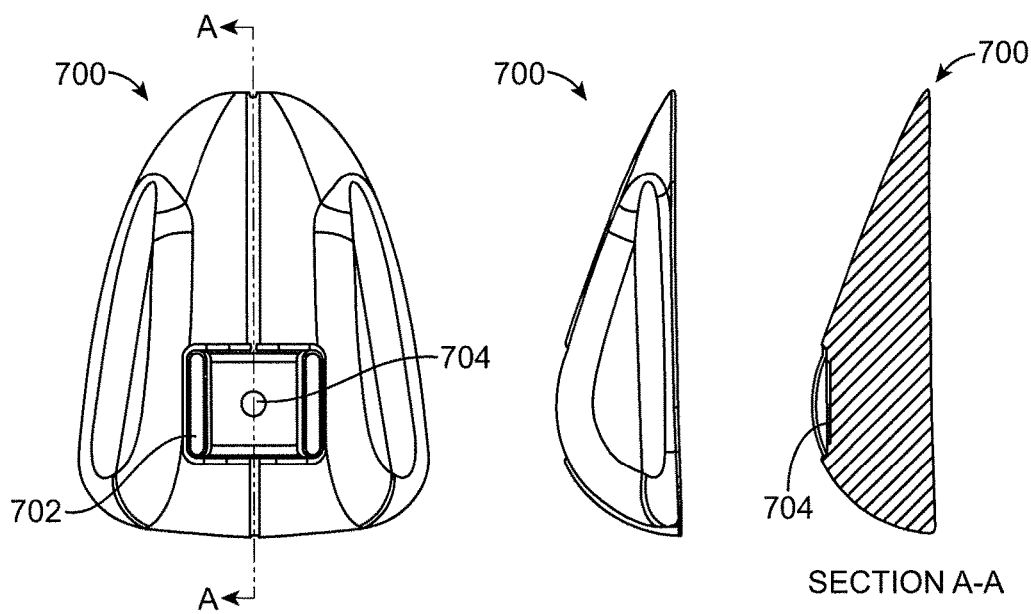
FIGS. 7A-7C illustrate various views of an embodiment of a hand support.

FIGS. 7A-7C illustrate an embodiment of a hand support 700 with an ergonomic shape that supports the palm of the hand in a relaxed, relatively unstressed configuration. The hand support 700 can have a pair of slots 702 for receiving a retaining member, such as a strap, that allows the hand support 700 to be removably and slidably secured to a base plate, such as the base plate illustrated in FIGS. 6A and 6B. An attachment feature 704 can be placed between the two slots 702 to removably secure the strap to the hand support 700. The attachment feature 704 can be a hook or loop type fastener that can attach to a complementary hook or loop type fastener on the strap. Other attachment features as described herein can also be used.

Figure 8A:
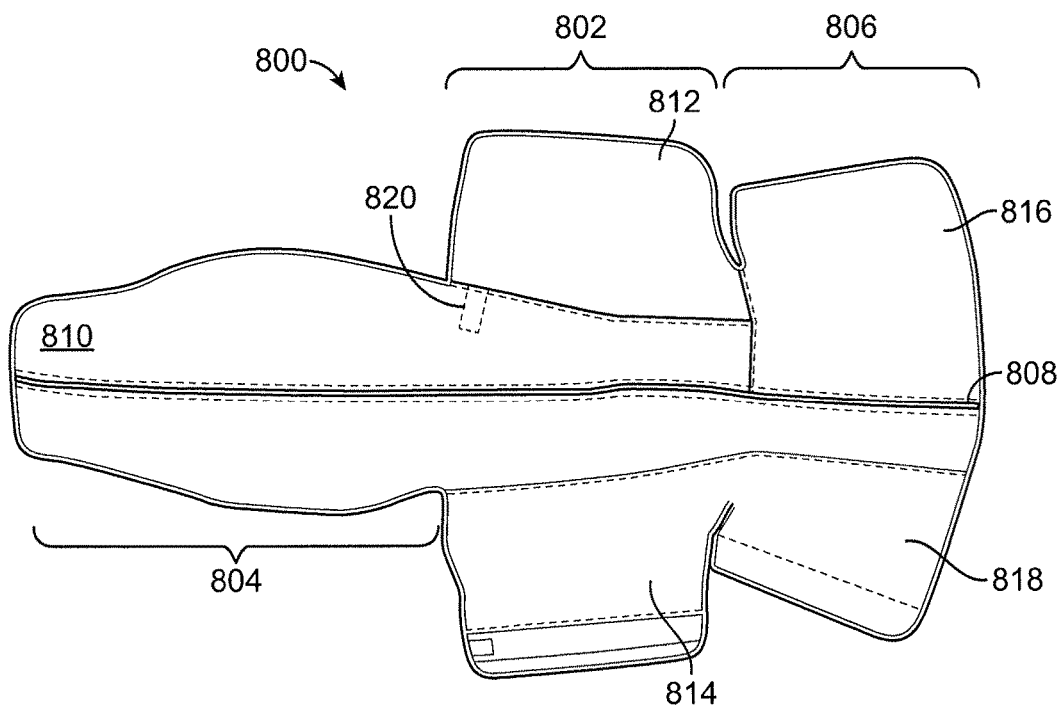
FIGS. 8A-8D illustrate an embodiment of a sleeve.

FIG. 8A illustrates the outside surface of an embodiment of the sleeve 800, which has a palm covering portion 802, a hand covering portion 804, and a forearm covering portion 806, all arranged along a longitudinal axis of the sleeve 800. A sealable opening 808 can be located on the outside surface 810 to allow a therapy component to be removable inserted into the sleeve. For example, the sealable opening 808 can be a zipper that runs along the longitudinal axis of the sleeve 800. Placing the zipper on the outside surface 810, rather than the inner skin facing surface, prevents irritation of the patient's skin from the irregular surface of the zipper when the sleeve is compressed around the patient's limb. The palm covering portion 802 can have a pair of wings 812, 814 that can be secured together or to another part of outer surface 810 of the sleeve, such as the outer surface of the hand covering portion 804, using an attachment feature, such as hook and loop fasteners. Similarly, the forearm covering portion 806 can also have a pair of wings 816, 818 that can be secured together or to another part of the outer surface 810 using an attachment feature.

Within the sleeve 800 can be an attachment feature 820 located on the inner surface of the outside surface 810 of the sleeve. For clarification, the inner surface referred to here does not refer to the skin contact surface of the sleeve, but instead refers to a surface within the pocket of the sleeve that opposes the outside surface 810. This attachment feature 820 within the pocket of the sleeve can be located in the palm covering portion 802 of the sleeve and can be a complementary attachment feature to the attachment feature 604 located on the bottom of the base plate 600 as described in FIGS. 6A and 6B. The attachment feature 820 within the inside of the palm cover portion 802 can be offset from the longitudinal axis and be positioned along a corner adjacent or near one of the wings 812, 814 and adjacent or near the hand covering portion 804. This offset arrangement of attachment features allows the base plate to be positioned correctly within the palm covering portion 802 in only one way.

Figure 8B:
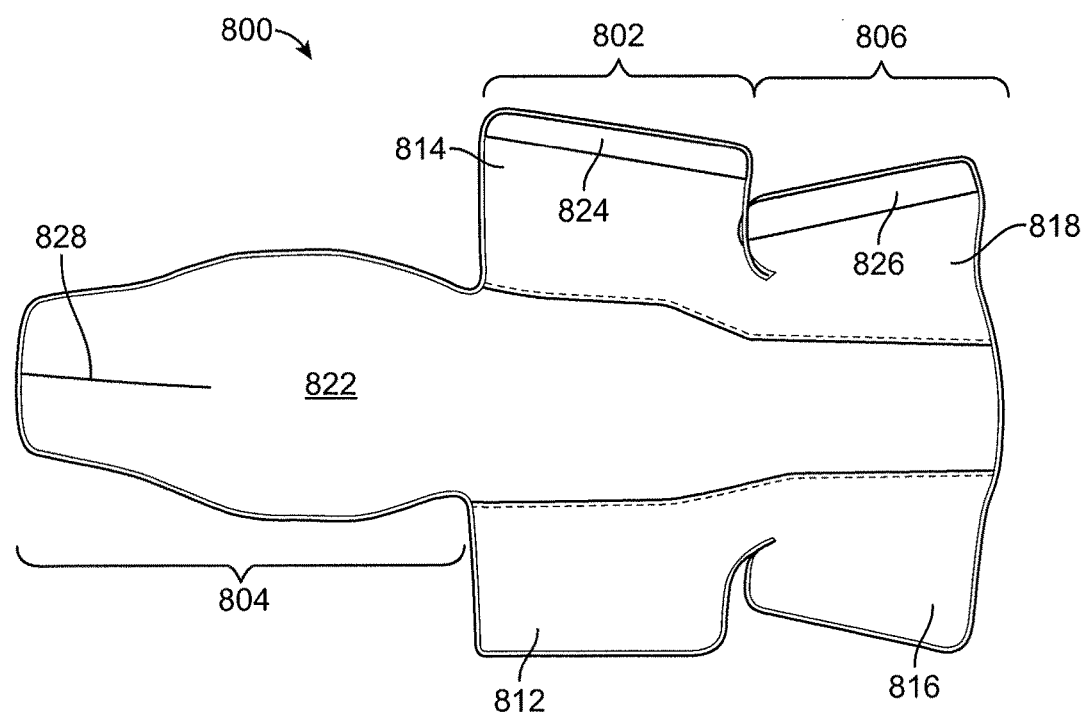

FIG. 8B shows the inside surface 822 of the sleeve that contacts the user's skin. An attachment feature 824, 826, such as a hook fastener, can be positioned along the outer edge of one wing from each pair of wings. A dart 828 or fold can extend from the end of the hand covering portion 804 along the longitudinal axis of the sleeve. The dart 828 can extend along a portion of the hand covering portion 804 to bias the hand covering portion 804 into a V or U shape that can fit more naturally over the dorsal aspect of the user's hand in the relaxed hand configuration. The dart 828 can extend about ¼ to the end of the hand covering portion 804.

Figure 8C:
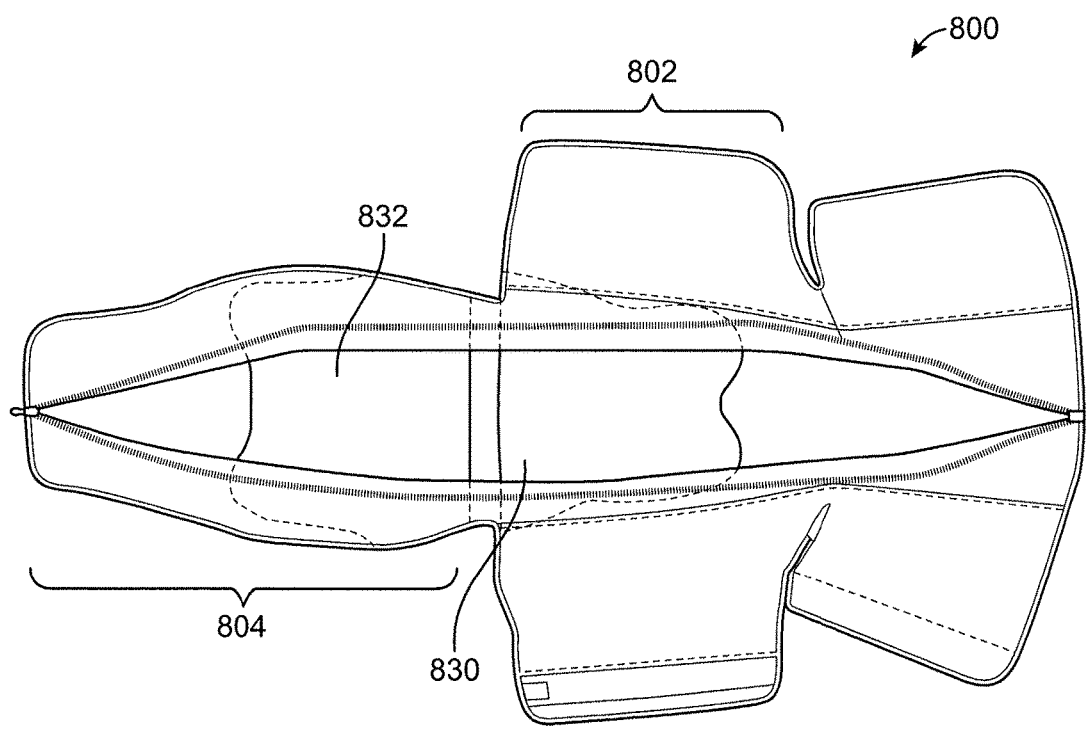

FIG. 8C illustrates two separate insulation members 830, 832 that can be attached within the palm covering portion 802 and the hand covering portion 804. The sides or outer edges of the insulation members 830, 832 can be attached to the sides or edges of the palm covering portion 802 or hand covering portion 804 while leaving the center portions of the insulation members free and unsecured. As a result, the insulation members 830, 832 divide at least parts of both the palm covering portion 802 and the hand covering portion 804 into two compartments, an inner skin facing compartment and an outer compartment. A therapy component can be inserted into either one of these compartments, allowing the user to insulate the therapy component or not to insulate the therapy component from the user's skin as needed. Separating the two insulating members 830, 832 may allow the hand covering portion 804 to be more easily folded over the palm covering portion 802 as compared to using a single insulation member that extends across both portions of the sleeve. In addition, separating the two insulating members allows the therapy component to be disposed in four different configurations: in both inner compartments, in both outer compartments, in the inner compartment of the palm covering portion and the outer compartment of the hand covering portion, and in the outer compartment of the palm covering portion and the inner compartment of the hand covering portion. A gap can be provide between the two insulation members at the transition area between the palm covering portion and the hand covering portion to facilitate folding between the two portions at the transition area.

Figure 8D:
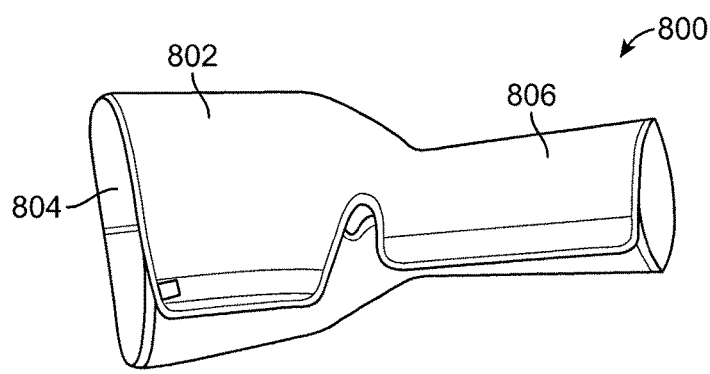

FIG. 8D illustrates the sleeve 800 in a folded configuration with the hand covering portion folded 804 over the palm covering portion 802, the wings of the palm covering portion 802 folded over the hand covering portion 804, and the wings of the forearm covering portion 806 folded over each other.

FIGS. 9A-9D illustrate the insertion of a therapy component 900, which can include a heat exchanger on one side and a gas bladder for compression on the other side, into the sleeve 800 shown if FIGS. 8A-8D. As shown in FIG. 9A, the sealable opening 808 of the sleeve 800, which can be a zipper, can be opened to provide access to the interior of the sleeve 800. FIG. 9B shows an embodiment of a therapy component 900 that can be inserted into the sleeve 800. The geometry of the therapy component 900 closely matches the interior geometry of the sleeve 800 such that therapy component 900 can fit snugly within the sleeve 800. The therapy component 900 can have a matching palm covering portion 902, a hand covering portion 904, and forearm covering portion 906. The wings 908, 910 of palm covering portion 902 can each be divided into two wings 908*a*, 908*b*, 910*a*, 910*b*, which may be asymmetric to each other, so that the wings wrapped more easily over the contours of the hand in its relaxed configuration. Similarly, the end of the hand covering portion 904 can be divided into two wings 904*a*, 904*b* that are configured to fit along each side of the dart 828 in the sleeve 800 shown in FIG. 8B, thereby allowing the end of the hand covering portion 904 to adopt the V or U shaped configuration of the corresponding sleeve portion.

FIGS. 9C-9D illustrate placing the therapy component 900 into the sleeve 800 such that the insulating members 830, 832 within the sleeve 800 are positioned between the therapy component 900 and the inside surface 822 of the sleeve 800 which contacts the patient's skin. In this configuration, at least a portion of the patient's hand, such as the fingers or the entire hand, can be insulated from the therapy component. Alternatively, as described above, the therapy component 900 can be positioned in other configurations with respect to the insulation members 830, 832. The hand covering portion 904 of the therapy component 900 can be inserted into the hand covering portion 804 of the sleeve, the subdivided wings 908, 910 of the palm covering portion 902 of the therapy component 900 can be inserted into corresponding wings 812, 814 of the palm covering portion 802 of the sleeve 800, and the wings 912, 914 of the forearm covering portion 906 of the therapy component 900 can be inserted into the corresponding wings 816, 818 of the forearm covering portion 806 of the sleeve 800. In addition, the heat exchanger side of the therapy component 900 can be facing the inside surface 822 of the sleeve 800 which contacts the patient's skin while the gas bladder for compression can be facing the outside surface 810 of the sleeve 800. Visual indicators can be used to help orient the therapy component 900 in the sleeve 800. For example, the visual indicators can be color coding between the sleeve 800 and therapy component 900. One example of color coding would be to match the color of the heat exchanger side of the therapy component 900 with the color of the inside surface 822 side of the sleeve 800, and to match the color of the gas bladder side of the therapy component 900 with the color of the outside surface 810 of the sleeve, with the two colors being different.

FIGS. 9E-9H illustrate the attachment of the base plate 600 to the hand support 700 illustrated in FIGS. 6A-7C. A removable retaining member 916, which can be a strap with hook fasteners on one side and loop fasteners on the other side, can be used to attach the base plate 600 to the hand support 700. The retaining member 916 can be threaded through and around the slots 602, 702 in both the base plate 600 and the hand support 700, and then secured to itself to form a loop around both the base plate 600 and the hand support 700, thereby securing the two parts together. The assembled based plate 600 and hand support 700 structure can then be inserted into the open sleeve 800 such that the attachment feature 604 on the bottom of the base plate 600 is removably attached to the corresponding attachment feature 820 within the sleeve 800, as discussed above. This positions the base plate 600 towards the outside surface of the sleeve 800 and the hand support 700 towards the inside surface of the sleeve. In addition, the tapering portion of the base plate 600 points towards the forearm covering portion of the sleeve 800. The sealable opening 808 can then be closed the complete the assembly of the therapy wrap. The therapy wrap formed by the sleeve 800 and therapy component 900 can then be folded over the patient's hand, wrist and forearm as shown in FIGS. 8D and 9I.

FIGS. 10A-D illustrate an embodiment of a reinforcement member 101 which can be disposed within the gas pressure bladder to prevent or reduce kinking in the gas bladder 38e. The reinforcement member 101 can be a foam or sponge-like material having an open cell or porous structure that is gas permeable and allows the passage of a gas through itself while keeping the gas bladder 38e open. In some embodiments, the reinforcement member can also be of a spacer fabric, mesh or non-porous material. The reinforcement member 101 can be positioned along locations which are prone to kinking, such as at portions of the wrap 30 that are folded or bent to conform to the patient's anatomy and/or to secure the wrap and/or are subject to flexure. For example, for a knee wrap, the portion of the wrap around the knee joint undergoes joint flexure, which can cause kinking of the wrap around the knee. By placing one or more reinforcement members 101 in the gas bladder around the portion of the wrap that is wrapped around the knee joint, kinking in the knee joint area is prevented or reduced by allowing the gas to vent thru the porous structural member, and/or around the edges of the structural member. Other kink prone areas include the transition area of the wrap between the main body portion of the wrap and the various arms and/or wings of the wrap. The performance may be further enhanced by providing the reinforcement member in most of or the entire portion of the wrap. Further benefit may be added if the structural member has insulating properties to reduce ambient heat transfer. Therefore, in some embodiments, the reinforcing member can be an insulator or an insulating material. In some embodiments, an insulating reinforcing member can have an adhesive coating at least the side of the reinforcing member facing the fluid bladder in order to improve contact between the insulating reinforcing member and the middle layer of the fluid bladder, thereby improving the insulation of the fluid bladder.

Figure 10E:
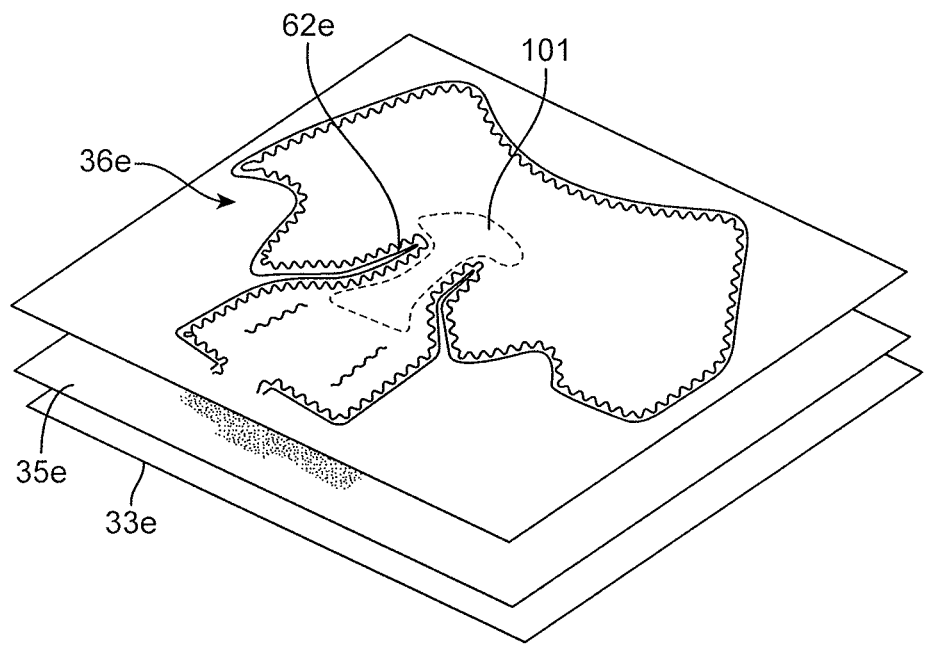
Figure 10F:
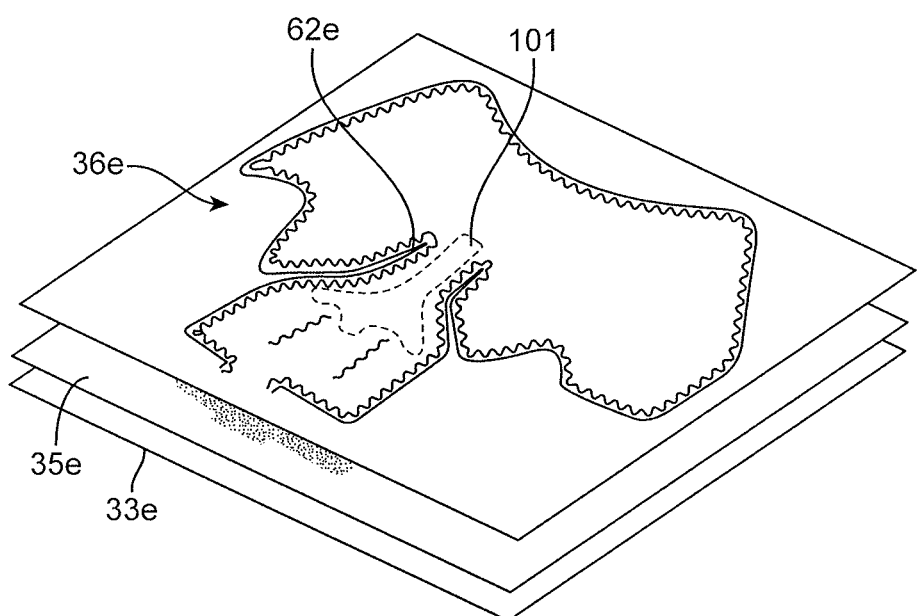

The reinforcement member 101 can be provided in a variety of shapes and sizes. For example, in some embodiments, the reinforcement member can be donut or washer shaped, such that the reinforcement member can have a center hole for attaching and securing the reinforcement member within the air bladder. For example, a spot weld can be placed within the center hole to secure the reinforcement member in place. In other embodiments, the reinforcement member can have other shapes, such as an hourglass shape, an oval shape, an arc shape, a wavy or undulating or sinusoidal shape, a generally curvilinear shape, for example, as illustrated in FIGS. 10E and 10F. In some embodiments, the shape of the reinforcement member is defined by the surrounding and/or underlying structures in the gas bladder and fluid bladder. For example, the perimeter or border in the gas bladder formed by the peripheral fence 62e can define a portion of the shape and size of the reinforcement member 101. In addition, interior fences 62e, which can be disposed within the gas bladder and/or the fluid bladder, can also define the shape and size of the reinforcement member 101. Other perimeter and interior features, such as attachment points and welds in the gas bladder and/or fluid bladder can also be used to define the size and shape of the reinforcement member. In other embodiments, the reinforcement member can be square, triangular, rectangular, hexagonal, or generally rectilinear shaped. In other embodiments, the reinforcement member can be shaped and sized to match the shape and size of the portion of the air bladder to be reinforced. These alternatively shaped reinforcement members can also have one or more holes so that the reinforcement member can be spot welded in place. In other embodiments, the reinforcement member can be spot welded or otherwise adhered or fastened directly to the layers that form the gas bladder rather than spot welding the layers together through a hole in the reinforcement member.

In some embodiments, the reinforcement member 101 can be substantially smaller than the air bladder such that a plurality of reinforcement members can be placed in the kink prone area of the air bladder. For example, the reinforcement member 101 can be less than $\frac{1}{3}$, $\frac{1}{4}$, $\frac{1}{5}$, or $\frac{1}{10}$ the width or length of the kink prone region of the air bladder. In other embodiments, the reinforcement member 101 can be approximately the same size as the kink prone region. In some embodiments, the width of the reinforcement member can be less than or approximately equal to the width of the spacing between the spot welds. In some embodiments, the width of the reinforcement member can be a multiple of the spacing distance between the spot welds.

Other techniques of fixing or staking the reinforcement member in place include use of adhesives, which can be used alone or be used in conjunction with the other forms of fixation, such as spot welding. When the adhesive is used in conjunction with another form of fixation, the adhesive may be tacky and provide releasable securement to allow repositioning of the reinforcement member before being permanently secured in place, if desired. Other fixation techniques include stitching, hook and loop fasteners, buttons, riveting, snaps, and the like. In some embodiments, the reinforcement member can be secured in place by placing fixation features around the perimeter of the reinforcement member. The fixation features can be spot welds or other guide members that hold the reinforcement member in place.

In some embodiments, the reinforcement member 101 can have a curved edge along the kink prone area in order to reduce formation of a kink along the edge of the reinforcement member 101. In some embodiments, a plurality of reinforcement members 101 can be disposed in the kink prone region. In some embodiments, the reinforcement members 101 can be disposed in a predetermined staggered or offset pattern along the kink prone region. In some embodiments, the reinforcement members can be disposed in one or more rows.

FIGS. 10B-10D illustrate one embodiment for fabricating a wrap 30 with reinforcement members 101 within the gas bladder 38e using a donut type reinforcement member 101 as described above. The first outer layer 33e and middle layer 35e can be assembled as described above to form the fluid bladder 37e. The reinforcement members 101 can then be placed at predetermined locations over remaining exposed surface of the middle layer 35e by centering the central hole of the reinforcement member 101 over placement markers, which can be weld dots in the flowpath. In some embodiments, the weld dots used as placement markers may be of different size than other weld dots, or may be of different color, or may have a marking to identify it as a placement marker. In some embodiments, a template can be used to place the reinforcement members at predetermined locations. In some embodiments, the template can have cutouts for receiving and placing the reinforcement members. In some embodiments, the reinforcement members 101 can be coated on one or both sides with a tacky adhesive that holds the reinforcement member 101 in place during the assembly process. After the reinforcement members 101 are placed, the third layer 36e can be placed over the middle layer 35e and reinforcement members to form the gas bladder 38e as described above. Welds can be made through the hole in the reinforcement member 101 to further secure the reinforcement member in place.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. For example, features described in one embodiment can be used in another embodiment. The embodiments were chosen and described in order to best explain the principles of the invention and its practical application, to thereby enable others skilled in the art to best utilize the invention and various embodiments with various modifications as are suited to the particular use contemplated.

What is claimed is:

1. A therapy wrap for treating a hand of a patient, the therapy wrap comprising:
    a sleeve comprising a palm facing portion, a forearm wrap portion and a hand covering portion;
    a hand support disposed within the palm facing portion of the sleeve, the hand support having a convex, curved palm facing surface configured to conform to a shape of the patient's hand in a relaxed state;
    a therapy component comprising a heat exchanger disposed in both the palm facing portion, the forearm wrap portion and the hand covering portion of the sleeve, the heat exchanger comprising a compliant fluid bladder; and
    a base plate having a slot wherein when the therapy wrap is in use treating the hand of a patient the therapy component is in the slot with the heat exchanger disposed in the hand covering portion on one side of the base plate and the heat exchanger disposed in the palm facing portion on another side of the base plate.

2. The therapy wrap of claim 1, wherein the base plate is configured to resist circumferential compression.

3. The therapy wrap of claim 1, wherein the base plate is made of a rigid material.

4. The therapy wrap of claim 1, wherein the hand support is made of a resilient material.

5. The therapy wrap of claim 1, wherein the hand support is made of a rigid material.

6. The therapy wrap of claim 4, wherein the resilient material is selected from the group consisting of a foam and a gel.

7. The therapy wrap of claim 1 wherein the slot in the base plate further comprises a retaining member with a curved surface.

8. The therapy wrap of claim 7, wherein a portion of the therapy component is disposed through the slot and wrapped around the curved surface of the retaining member when the therapy component is in a folded configuration.

9. The therapy wrap of claim 1, wherein the hand support is slidably secured to the base plate.

10. The therapy wrap of claim 1, wherein the hand support is removably secured to the base plate.

11. The therapy wrap of claim 1, wherein the base plate is attached to the palm facing portion of the sleeve.

12. The therapy wrap of claim 1, wherein the therapy component further comprises an air bladder.

13. The therapy wrap of claim 12, wherein the air bladder is positioned on an outer portion of the therapy component and the heat exchanger is positioned on an inner portion of the therapy component, wherein the inner portion of the therapy component is configured to face the patient's hand.

14. The therapy wrap of claim 12, wherein the air bladder comprises one or more reinforcement members located along portions of the air bladder that are configured to fold.

15. The therapy wrap of claim 14, wherein the one or more reinforcement members are made of foam.

16. The therapy wrap of claim 12 wherein the base plate is attached directly to the air bladder.

17. The therapy wrap of claim 12 wherein the base plate is attached to a perimeter of the heat exchanger.

18. The therapy wrap of claim 1, wherein the therapy component further comprises an air bladder, wherein in use the air bladder provides circumferential compression in the forearm wrap portion.

19. The therapy wrap of claim 1, wherein the hand support is coupled to the base plate within the palm facing portion of the therapy component.

20. The therapy wrap of claim 19, wherein the base plate extends into the forearm wrap portion.

21. The therapy wrap of claim 19, further comprising a tether between the hand support and the base plate.

22. The therapy wrap of claim 19, further comprising a groove in the base plate sized and positioned to receive the hand support and allow the hand support to slide relative to the base plate along the groove.

23. The therapy wrap of claim 19, further comprising a pair of grooves in the base plate sized and positioned to receive the hand support and allow the hand support to slide relative to the base plate along the pair of grooves.

24. The therapy wrap of claim 1, wherein the palm facing portion has a first pair of wings and the forearm wrap portion has a second pair of wings.

25. The therapy wrap of claim 1, further comprising a thermal insulating member disposed in a portion of the palm facing portion of the sleeve.

26. The therapy wrap of claim 25, wherein the thermal insulating member extends into the hand covering portion of the sleeve.

27. The therapy wrap of claim 25, further comprising a second thermal insulating member disposed in the hand covering portion of the sleeve.

28. The therapy wrap of claim 25, wherein the thermal insulating member is removably attached to the sleeve.

29. The therapy wrap of claim 25, wherein the thermal insulting member is attached within the sleeve to divide the palm facing portion into a skin facing compartment and an outer compartment, wherein both the skin facing compartment and the outer compartment are configured to removably receive the therapy wrap.

30. A method for treating a hand of a patient, the method comprising:
    wrapping a hand and a forearm of the patient with a sleeve such that the patient's palm is facing a palm facing portion of the sleeve and the patient's forearm is in a forearm portion of the sleeve;
    folding a hand covering portion of the sleeve over the back of the patient's hand;
    conforming the patient's hand in a relaxed state to a hand support disposed within the palm facing portion of the sleeve, the hand support having a convex, curved palm facing surface; and circulating a heat exchange fluid through a therapy component comprising a heat exchanger disposed in the palm facing portion, the forearm portion and the hand covering portion of the sleeve, wherein the therapy component is received within a slot provided on a base plate such that the heat exchanger is disposed on the hand covering portion on one side of the base plate and the heat exchanger is disposed on the palm facing portion on another side of the slot base plate.

31. The method of claim 30, further comprising applying a flat pressure to the palm and the back of the patient's hand by inflating an air bladder that forms a part of the therapy component.

32. The method of claim 31, wherein the base plate resists circumferential compression of the patient's hand.

33. The method of claim 30, further comprising operating the therapy component to apply a circumferential pressure to the patient's forearm.

34. The method of claim 30, further comprising positioning a thermal insulating member between the patient's fingers and the therapy component.

35. The method of claim 34, wherein the thermal insulating member is removably placed.

36. The method for treating a hand of claim 30 the folding step further comprising:
 folding the hand covering portion of the sleeve about the base plate beneath the hand support.

37. The method for treating a hand of claim 30 further comprising: moving the hand support along a tether to adjust the position of the hand support relative to the patient's hand.

38. The method for treating a hand of claim 30 further comprising: moving the hand support along two or more slots to adjust the position of the hand support relative to the patient's hand.

* * * * *